United States Patent
Kunugi et al.

(10) Patent No.: US 11,655,493 B2
(45) Date of Patent: May 23, 2023

(54) BIOMARKER FOR MENTAL DISEASE

(71) Applicants: NATIONAL CENTER OF NEUROLOGY AND PSYCHIATRY, Kodaira (JP); KABUSHIKI KAISHA YAKULT HONSHA, Tokyo (JP)

(72) Inventors: Hiroshi Kunugi, Kodaira (JP); Emiko Aizawa, Kodaira (JP); Hirokazu Tsuji, Funabashi (JP)

(73) Assignees: NATIONAL CENTER OF NEUROLOGY AND PSYCHIATRY, Kodaira (JP); KABUSHIKI KAISHA YAKULT HONSHA, Tokyo (JP)

( * ) Notice: Subject to any disclaimer, the term of this patent is extended or adjusted under 35 U.S.C. 154(b) by 561 days.

(21) Appl. No.: 15/566,290

(22) PCT Filed: Apr. 15, 2016

(86) PCT No.: PCT/JP2016/062182
§ 371 (c)(1),
(2) Date: Oct. 13, 2017

(87) PCT Pub. No.: WO2016/167365
PCT Pub. Date: Oct. 20, 2016

(65) Prior Publication Data
US 2018/0100177 A1  Apr. 12, 2018

(30) Foreign Application Priority Data

Apr. 16, 2015 (JP) ................. JP2015-083936

(51) Int. Cl.
| | |
|---|---|
| *C12Q 1/06* | (2006.01) |
| *A61K 45/00* | (2006.01) |
| *G01N 33/569* | (2006.01) |
| *C12Q 1/689* | (2018.01) |
| *C12Q 1/6883* | (2018.01) |
| *G01N 33/15* | (2006.01) |
| *C12Q 1/10* | (2006.01) |
| *C12Q 1/14* | (2006.01) |
| *G01N 33/487* | (2006.01) |
| *C12N 1/20* | (2006.01) |
| *C12Q 1/68* | (2018.01) |

(52) U.S. Cl.
CPC ............. *C12Q 1/06* (2013.01); *A61K 45/00* (2013.01); *C12Q 1/10* (2013.01); *C12Q 1/14* (2013.01); *C12Q 1/689* (2013.01); *C12Q 1/6883* (2013.01); *G01N 33/15* (2013.01); *G01N 33/48735* (2013.01); *G01N 33/56911* (2013.01); *G01N 33/56916* (2013.01); *C12N 1/20* (2013.01); *C12Q 1/68* (2013.01); *G01N 2800/065* (2013.01); *G01N 2800/302* (2013.01); *G01N 2800/304* (2013.01)

(58) Field of Classification Search
CPC ... A61K 45/00; A61P 1/00; A61P 1/12; A61P 25/18; A61P 25/24; C12N 1/20; C12Q 1/06; C12Q 1/10; C12Q 1/14; C12Q 1/68; C12Q 1/6883; C12Q 1/689; G01N 2800/065; G01N 2800/302; G01N 2800/304; G01N 33/15; G01N 33/48735; G01N 33/56911; G01N 33/56916
See application file for complete search history.

(56) References Cited

FOREIGN PATENT DOCUMENTS

| | | |
|---|---|---|
| EP | 1 997 905 A1 | 12/2008 |
| EP | 1 997 906 A1 | 12/2008 |
| EP | 1 997 907 A1 | 12/2008 |
| RU | 2 311 126 C1 | 11/2007 |

OTHER PUBLICATIONS

Mikelsaar et al. Adv Exp Med Biol—Advances in Microbiology, Infectious Diseases and Public Health (2016) 4: 1-64 (Year: 2016).*
Supplementary Partial European Search Report dated Sep. 4, 2018 in Patent Application No. 16780156.2, 16 pages.
Logan, A C. et al., "Major depressive disorder: probiotics may be an adjuvant therapy" Medical Hypotheses, vol. 64, No. 3, XP002534278, 2005, pp. 533-538.
Extended European Search Report dated Nov. 21, 2018 in European Patent Application No. 16780156.2, 15 pages.
Maukonen, J. et al. "Prevalence and temporal stability of selected clostridial groups in irritable bowel syndrome in relation to predominant faecal bacteria", Journal of Medical Microbiology, XP055523180, vol. 55, No. 5, 2006, pp. 625-633.
International Search Report dated Jun. 14, 2016, in PCT/JP2016/062182 filed Apr. 15, 2016.
Messaoudi et al., "Beneficial psychological effects of a probiotic formulation (*Lactobacillus helveticus* R0052 and *Bifidobacterium longum* R0175) in healthy human volunteers", Gut Microbes, vol. 2, Issue 4, (2011), pp. 256-261, 7 pages.
Kinross et al., "Gut microbiome-host interactions in health and disease", Genome Medicine, vol. 3, No. 14, (2011), 12 pages.
Kunugi, "Stress and Enterobacteria", Journal of the Japanese Association of Stress Science, vol. 29, No. 2, ISSN 1349-4813, (2014), with partial English translation, 6 pages.
Kunugi, "Stress and Enterobacteria", 30th Anniversary Meeting of the Japanese Association of Stress Science, (2014), with partial English Translation, 4 pages.

(Continued)

*Primary Examiner* — Blaine Lankford
(74) *Attorney, Agent, or Firm* — Oblon, McClelland, Maier & Neustadt, L.L.P.

(57) ABSTRACT

A marker for determining a mental disease is provided. The marker can be used in an objective diagnosis of such a mental disease. The marker contains one or more enterobacteria of *Bifidobacterium, Lactobacillus, Lactobacillus brevis, Lactobacillus reuteri* subgroup, *Lactobacillus sakei* subgroup, *Atopobium* cluster, *Bacteroides fragilis* group, *Enterococcus, Clostridium coccoides* group, *Clostridium leptum* subgroup, *Staphylococcus, Clostridium perfringens,* and *Enterobacteriaceae*.

5 Claims, 4 Drawing Sheets
Specification includes a Sequence Listing.

(56) References Cited

OTHER PUBLICATIONS

Kunugi, "Relationship between enterobacteria and mental disease, which has been started to be elucidated", Medical Tribune, (2015), with partial English translation, 6 pages.
Kunugi, "Clinical Nutriology of the Mind", Japanese Journal of Clinical Psychology, vol. 15, No. 1, (2015), with partial English Translation, 15 pages.
Sudo, "Effects of gut microbiota on psychological development and mental health", Journal of Clinical and Experimental Medicine (Igaku No Ayumi), vol. 243, No. 2, (2012), with partial English translation, 6 pages.
Fujita, "The immunology of mind and body: the activity of the intestinal bacteria", The Japan Society of Health Sciences of Mind and Body, vol. 8, No. 2, (2012), with partial English Translation, 6 pages.
Sudo, "Enterobacteria and stress response", Microbiome-Gut-Brain Axis, vol. 22, No. 2, (2014), with partial English Translation, 9 pages.
Grenham et al., "Brain-gut-microbe communication in health and disease", Frontiers in Physiology, vol. 2, Article 94, (2011), pp. 1-15.
Office Action dated Mar. 26, 2021 for Chinese Patent Application No. 201680021725.6 (with machine translation), 23 pages.
Liang Shan, et al., "Microbes and Behavior and X Mental Illness", Advances in Psychological Science, Jan. 31, 2012, vol. 20, No. 1, 75 and 82-84 (with partial machine translation) 7 pages.
Kazunori Matsuda, et al., "Establishment of an Analytical System for the Human Fecal Microbiota, Based on Reverse Transcription-X Quantitative PCR Targeting of Multicopy rRNA Molecules", Applied and Environmental Microbiology, vol. 75, No. 7, Feb. 5, 2009, pp. 1961-1963.

* cited by examiner

BIOMARKER FOR MENTAL DISEASE

FIELD OF THE INVENTION

The present invention relates to a marker for determining a mental disease, which is capable of simply, conducting examinations.

BACKGROUND OF THE INVENTION

In the modern society, various factors cause stress, and such stress induces a mental disease in many cases. According to WHO International Classification of Diseases, 10th Revision (ICD-10), mental diseases are classified into 10 types 1 classification, and such mental diseases include various diseases such as dementia, schizophrenia, and mood disorder. Heredity and, environment (stress) are considered to be very important risk factors for the development of these mental diseases. In recent years, the number of patients with mental diseases has tended to increase over the world, and has become a major social problem.

Among mental diseases, depression, manic depression, and schizophrenia have a large number of patients, and thus, a large number of related studies have been conducted on these diseases.

Depression is characterized in that it has a combination of symptoms such as low mood, loss of energy, loss of interest, sensation attended with physical disease, poor concentration, changes in appetite, changes in sleeping, and decreases in physical function and mental function, and this is a disorder providing a sense of helplessness, a sense of anxiety, etc.

Manic depression is a disease in which a manic state, which is completely opposite to a depressive state, appears in addition to the depressive state, and the two states appear repeatedly. Manic depression is also referred to as bipolar disorder.

Schizophrenia is characterized in that it has positive symptoms such as auditory hallucination or delusion, and negative symptoms such as loss of motivation or slowdown in emotion.

The diagnosis of these mental diseases is carried out based on the interview with a patient, and in some cases, also based on information obtained from the patient's family, by using, as determination criteria, WHO International Classification of Diseases, 10th Revision, or "Diagnostic and Statistical Manual of Mental Disorders, 5th Edition (DSM-5) developed by American Psychiatric Association (APA). However, the final decision must be relied on the subjectivity of a doctor in charge, based on the doctor's experience, and thus, the accuracy of the diagnosis has not yet been sufficient from the viewpoint of objective diagnosis.

Meanwhile, in studies regarding the relation of enterobacteria with mental symptoms, it has been known that when *Lactobacillus helveticus* R0052 and *Bifidobacterium longum* R0175 have been administered to healthy subjects, amelioration of anxiety, depression and the like has been recognized according to self-diagnosis (Non Patent Literature 1), and that *Clostridium bolteae* is present in the intestine of children with autism at a high frequency (Non Patent Literature 2). However, findings regarding determination of a mental disease using enterobacteria have not yet been known.

CITATION LIST

Non Patent Literature

Non Patent Literature 1: Michael et. al., Gut Microbes 2: 4, 256-261, 2011

Non Patent Literature 2: Kinross et. al., Genome Medicine 2011, 3: 14

SUMMARY OF THE INVENTION

Problems to be Solved by the Invention

As mentioned above, the diagnosis of a mental disease still depends on the subjectivity of a doctor in charge, which is based on the experience of the doctor, and thus, the accuracy of the diagnosis has not yet been sufficient.

Accordingly, it is an object of the present invention to provide a novel marker for determining a mental disease, which is more objective, simple, and non-invasive.

Means for Solving the Problems

Hence, the present inventors have focused on enterobacteria, and have studied regarding the availability of the enterobacteria for determination of a mental disease. As a result, the present inventors have found: that specific enterobacteria, which are different from conventionally known enterobacteria, have a correlation with various mental diseases; that the presence or absence of a mental disease and/or the severity of such a mental disease can be determined by examining the presence or absence of such enterobacteria or the number of cells thereof; and further that a prophylactic or therapeutic agent for mental diseases can be selected through screening by employing such enterobacteria as indices, thereby completing the present invention.

Specifically, the present invention provides the following [1] to [21].

[1] A marker for determining a mental disease, comprising one or more enterobacteria selected from the group consisting of *Bifidobacterium, Lactobacillus, Lactobacillus brevis, Lactobacillus reuteri* subgroup, *Lactobacillus sakei* subgroup, *Atopobium* cluster, *Bacteroides fragilis* group, *Enterococcus, Clostridium coccoides* group, *Clostridium leptum* subgroup, *Staphylococcus, Clostridium perfringens* and *Enterobacteriaceae*.

[2] The marker according to the above [1], wherein the determination of a mental disease is determination of the presence or absence of a mental disease and/or the severity of a mental disease.

[3] The marker according to the above [2], wherein the mental disease is one or more selected from the group consisting of depression, manic depression and schizophrenia.

[4] A method of measuring one or more enterobacteria selected from the group consisting of *Bifidobacterium, Lactobacillus, Lactobacillus brevis, Lactobacillus reuteri* subgroup, *Lactobacillus sakei* subgroup, *Atopobium* cluster, *Bacteroides fragilis* group, *Enterococcus, Clostridium coccoides* group, *Clostridium leptum* subgroup, *Staphylococcus, Clostridium perfringens* and *Enterobacteriaceae* contained in a specimen, for use in determining a mental disease.

[5] The method according to the above [4], wherein the determination of a mental disease is determination of the presence or absence of a mental disease and/or the severity of a mental disease.

[6] The method according to the above [5], wherein the mental disease is one or more selected from the group consisting of depression, manic depression and schizophrenia.

[7] The method according to any one of the above [4] to [6], wherein the specimen is feces of a subject.

[8] A kit for carrying out a measurement method according to any one of the above [4] to [7], comprising a reagent for measuring enterobacteria according to any one of the above [1] to [3] contained in a specimen and a protocol.
[9] The kit according to the above [8], wherein the specimen is feces of a subject.
[10] A screening method for a mental disease-improving agent, comprising employing, as an index, a variation in the number of enterobacterial cells according to any one of the above [1] to [3].
[11] The screening method according to the above [10], wherein the mental disease is one or more selected from the group consisting of depression, manic depression and schizophrenia.
[12] A mental disease-improving agent obtained by a method according to the above [10] or [11].
[13] A marker for determining irritable bowel syndrome in a manic depression patient, comprising one or more enterobacteria selected from the group consisting of *Atopobium* cluster, *Clostridium coccoides* group and *Staphylococcus*.
[14] The marker according to the above [13], wherein the determination of irritable bowel syndrome is determination of the presence or absence of irritable bowel syndrome and/or the severity of irritable bowel syndrome.
[15] A method of measuring one or more enterobacteria selected from the group consisting of *Atopobium* cluster, *Clostridium coccoides* group and *Staphylococcus* contained in a specimen, for use in determining irritable bowel syndrome in a manic depression patient.
[16] The method according to the above [15], wherein the determination of irritable bowel syndrome is determination of the presence or absence of irritable bowel syndrome and/or the severity of irritable bowel syndrome.
[17] The method according to the above [15] or [16], wherein the specimen is feces of a manic depression patient.
[18] A kit for carrying out a measurement method according to any one of the above [15] to [17], comprising a reagent for measuring enterobacteria according to the above [13] or [14] contained in a specimen and a protocol.
[19] The kit according to the above [18], wherein the specimen is feces of a manic depression patient.
[20] A screening method for an agent for treating irritable bowel syndrome in a manic depression patient, comprising employing, as an index, a variation in the number of enterobacterial cells according to the above [13] or [14].
[21] An agent for treating irritable bowel syndrome in a manic depression patient, which is obtained by a method according to the above [20].

Effects of the Invention

By measuring the determination marker of the present invention, the presence or absence of a mental disease such as depression, manic depression or schizophrenia, and/or the severity of such a mental disease can be simply and non-invasively determined. In addition, the presence or absence of irritable bowel syndrome and/or the severity thereof in a depression patient can also be determined. Moreover, by using the determination marker of the present invention as an index, a mental disease-improving agent can be selected through screening.

MODES FOR CARRYING OUT THE INVENTION

Figure 1:
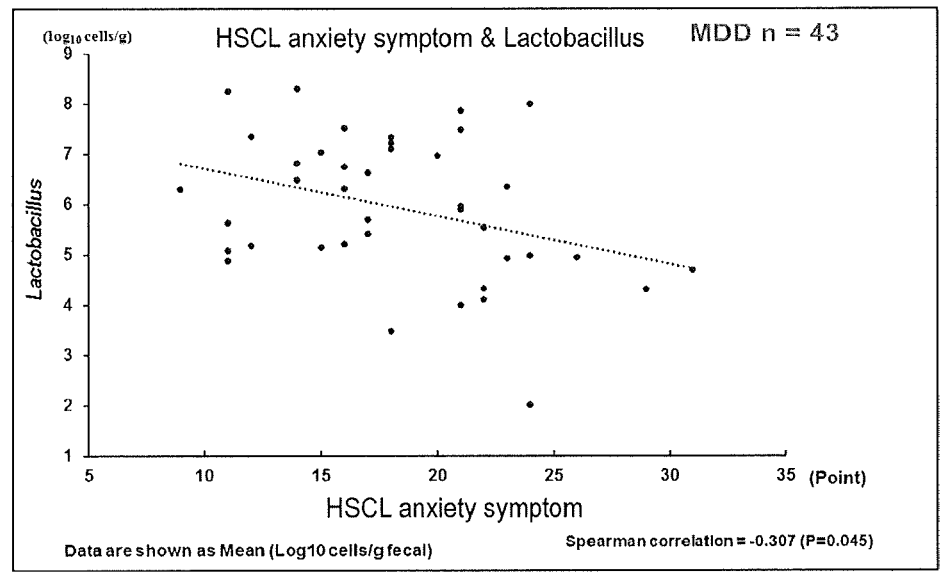
FIG. 1 shows a correlation between the number of cells of *Lactobacillus* in depression patients and the score of anxiety symptom according to the Hopkins Symptom Checklist (HSCL), a self-report measure of stress. The higher the severity, the smaller the number of cells. In contrast, the lower the severity, the larger the number of cells.

The marker for determining a mental disease of the present invention comprises one or more enterobacteria selected from the group consisting of *Atopobium* cluster, *Lactobacillus, Lactobacillus brevis, Lactobacillus reuteri* subgroup, *Lactobacillus sakei* subgroup, *Bifidobacterium, Bacteroides fragilis* group, *Enterococcus, Clostridium coccoides* group, *Clostridium leptum* subgroup, *staphylococcus, Clostridium perfringens* and *Enterobacteriaceae*. These enterobacteria have been known to be present in the intestine of humans. However, there have been no reports regarding the relationship of these enterobacteria with mental diseases. The term "*Lactobacillus*" is used herein to mean the whole bacteria belonging to the genus *Lactobacillus*, and the terms "*Lactobacillus reuteri* subgroup" and "*Lactobacillus sakei* subgroup" are used herein to mean bacteria belonging to such groups.

As described in the later-mentioned test examples, a significant correlation has been found between the number of the above described enterobacterial cells in the feces of a patient with a mental disease, and the mental disease. More specifically, a significant correlation has been found between the number of the above described enterobacterial cells, and the presence or absence of a mental disease and/or the severity of such a mental disease.

Herein, the term "mental disease" includes one or more selected from the group consisting of depression, manic depression and schizophrenia.

More specifically, the relationship between enterobacteria and a mental disease is as follows.

1. *Atopobium* Cluster (1) Depression

The number of cells of *Atopobium* cluster in a depression patient is significantly smaller than that in a healthy subject. Specifically, when the number of cells of *Atopobium* cluster per 1 g of specimen is less than $10^{9.5}$ cells, it can be determined that the subject is highly likely to have depression.

(2) Schizophrenia

The number of cells of *Atopobium* cluster in a schizophrenia patient is significantly smaller than that in a healthy subject. Specifically, when the number of cells of *Atopobium* cluster per 1 g of specimen is less than $10^{9.5}$ cells, it can be determined that the subject is highly likely to have schizophrenia.

2. *Lactobacillus*

(1) Depression

The number of cells of *Lactobacillus* in a depression patient is significantly smaller than that in a healthy subject. Specifically, when the number of cells of *Lactobacillus* per 1 g of specimen is less than $10^{6.5}$ cells, it can be determined that the subject is highly likely to have depression.

Moreover, there is a significant correlation, such that the higher the score of anxiety symptom according to the self-report measure of stress, the smaller the number of cells of *Lactobacillus*, whereas the lower the symptom or the score, the larger the number of cells of *Lactobacillus*. Thus, the severity of depression can be determined using the number of cells of *Lactobacillus*. Specifically, regarding anxiety symptom, it can be determined that when the number of cells of *Lactobacillus* is $10^{6.5}$ cells or more per 1 g of specimen, the subject is highly likely to have a mild degree of anxiety symptom, that when the number of cells of *Lactobacillus* is $10^{6.4}$ to $10^{5.8}$ cells per 1 g of specimen, the subject is highly likely to have a moderate degree of anxiety symptom, and that when the number of cells of *Lactobacillus* is $10^{5.7}$ cells or less per 1 g of specimen, the subject is highly likely to have a severe degree of anxiety symptom.

3. *Lactobacillus Brevis*

(1) Depression

The number of cells of *Lactobacillus brevis* in a depression patient is significantly smaller than that in a healthy subject. Specifically, when the number of cells of *Lactobacillus brevis* per 1 g of specimen is less than $10^{3.7}$ cells, it can be determined that the subject is highly likely to have depression.

(2) Manic Depression

The number of cells of *Lactobacillus brevis* in a manic depression patient is significantly smaller than that in a healthy subject. Specifically, when the number of cells of *Lactobacillus brevis* per 1 g of specimen is less than $10^{4.0}$ cells, it can be determined that the subject is highly likely to have manic depression.

(3) Schizophrenia

The number of cells of *Lactobacillus brevis* in a schizophrenia patient is significantly smaller than that in a healthy subject. Specifically, when the number of cells of *Lactobacillus brevis* per 1 g of specimen is less than $10^{4.0}$ cells, it can be determined that the subject is highly likely to have schizophrenia.

4. *Lactobacillus Reuteri* Subgroup (1) Depression

The number of cells of *Lactobacillus reuteri* subgroup in a depression patient is significantly smaller than that in a healthy subject. Specifically, when the number of cells of *Lactobacillus reuteri* subgroup per 1 g of specimen is less than $10^{4.7}$ cells, it can be determined that the subject is highly likely to have depression.

(2) Manic Depression

The number of cells of *Lactobacillus reuteri* subgroup in a manic depression patient is significantly smaller than that in a healthy subject. Specifically, when the number of cells of *Lactobacillus reuteri* subgroup per 1 g of specimen is less than $10^{4.8}$ cells, it can be determined that the subject is highly likely to have manic depression.

(3) Schizophrenia

The number of cells of *Lactobacillus reuteri* subgroup in a schizophrenia patient is significantly smaller than that in a healthy subject. Specifically, when the number of cells of *Lactobacillus reuteri* subgroup per 1 g of specimen is less than $10^{4.8}$ cells, it can be determined that the subject is highly likely to have schizophrenia.

5. *Lactobacillus Sakei* Subgroup (1) Schizophrenia

The number of cells of *Lactobacillus sakei* subgroup in a schizophrenia patient is significantly smaller than that in a healthy subject. Specifically, when the number of cells of *Lactobacillus sakei* subgroup per 1 g of specimen is less than $10^{4.8}$ cells, it can be determined that the subject is highly likely to have schizophrenia.

6. *Bifidobacterium*

(1) Depression

The number of cells of *Bifidobacterium* in a depression patient is significantly smaller than that in a healthy subject. Specifically, when the number of cells of *Bifidobacterium* per 1 g of specimen is less than $10^{10.1}$ cells, it can be determined that the subject is highly likely to have depression.

Moreover, as the number of cells of *Bifidobacterium* has increased in a depression patient, the depressive symptom of the patient has tended to be alleviated.

(2) Manic Depression

The number of cells of *Bifidobacterium* is useful for determination of the severity of a manic depression patient. In the evaluation according to the HSCL, a self-report measure of stress, as the scores of obsessive symptom, interpersonal hypersensitivity, anxiety symptom, depressive symptom and total score have increased in a manic depression patient, the number of cells of *Bifidobacterium* has decreased. In contrast, as the above described scores have decreased, the number of cells of *Bifidobacterium* has increased. Thus, there is a significant correlation between them.

Specifically, regarding obsessive symptom, it can be determined that when the number of cells of *Bifidobacterium* is $10^{9.9}$ cells or more per 1 g of specimen, the subject is highly likely to have a mild degree of obsessive symptom, that when the number of cells of *Bifidobacterium* is $10^{9.8}$ to $10^{9.5}$ cells per 1 g of specimen, the subject is highly likely to have a moderate degree of obsessive symptom, and that when the number of cells of *Bifidobacterium* is $10^{9.4}$ cells or less per 1 g of specimen, the subject is highly likely to have a severe degree of obsessive symptom. Regarding interpersonal hypersensitivity, it can be determined that when the number of cells of *Bifidobacterium* is $10^{10.1}$ cells or more per 1 g of specimen, the subject is highly likely to have a mild degree of interpersonal hypersensitivity, that when the number of cells of *Bifidobacterium* is $10^{10.0}$ to $10^{9.9}$ cells per 1 g of specimen, the subject is highly likely to have a moderate degree of interpersonal hypersensitivity, and that when the number of cells of *Bifidobacterium* is $10^{9.8}$ cells or less per 1 g of specimen, the subject is highly likely to have a severe degree of interpersonal hypersensitivity. Regarding anxiety symptom, it can be determined that when the number of cells of *Bifidobacterium* is $10^{9.7}$ cells or more per 1 g of specimen, the subject is highly likely to have a mild degree of anxiety symptom, that when the number of cells of *Bifidobacterium* is $10^{9.6}$ to $10^{9.3}$ cells per 1 g of specimen, the subject is highly likely to have a moderate degree of anxiety symptom, and that when the number of cells of *Bifidobacterium* is $10^{9.2}$ cells or less per 1 g of specimen, the subject is highly likely to have a severe degree of anxiety symptom. Regarding depressive symptom, it can be determined that when the number of cells of *Bifidobacterium* is $10^{9.9}$ cells or more per 1 g of specimen, the subject is highly likely to have a mild degree of depressive symptom, that when the number of cells of *Bifidobacterium* is $10^{9.8}$ to $10^{9.4}$ cells per 1 g of specimen, the subject is highly likely to have a moderate degree of depressive symptom, and that when the number of cells of *Bifidobacterium* is $10^{9.3}$ cells or less per 1 g of specimen, the subject is highly likely to have a severe degree of depressive symptom.

7. *Bacteroides Fragilis* Group (1) Schizophrenia

The number of cells of *Bacteroides fragilis* group in a schizophrenia patient is significantly smaller than that in a healthy subject. Specifically, when the number of cells of *Bacteroides fragilis* group per 1 g of specimen is less than $10^{9.1}$ cells, it can be determined that the subject is highly likely to have schizophrenia.

8. *Enterococcus*

(1) Depression

The number of cells of *Enterococcus* in a depression patient is significantly smaller than that in a healthy subject. Specifically, when the number of cells of *Enterococcus* per 1 g of specimen is less than $10^{7.1}$ cells, it can be determined that the subject is highly likely to have depression.

(2) Manic Depression

The number of cells of *Enterococcus* in a manic depression patient is significantly larger than that in a healthy subject. Specifically, when the number of cells of *Enterococcus* per 1 g of specimen is $10^{5.0}$ cells or more, it can be determined that the subject is highly likely to have manic depression.

9. *Clostridium Coccoides* Group (1) Depression

The number of cells of *Clostridium* coccoides group in a depression patient is significantly larger than that in a healthy subject. Specifically, when the number of cells of *Clostridium* coccoides group per 1 g of specimen is $10^{10.3}$ cells or more, it can be determined that the subject is highly likely to have depression.

(2) Manic Depression

The number of cells of *Clostridium coccoides* group in a manic depression patient is significantly smaller than that in a healthy subject. Specifically, when the number of cells of *Clostridium coccoides* group per 1 g of specimen is less than $10^{9.3}$ cells, it can be determined that the subject is highly likely to have manic depression.

(3) Schizophrenia

The number of cells of *Clostridium coccoides* group in a schizophrenia patient is significantly smaller than that in a healthy subject. Specifically, when the number of cells of *Clostridium coccoides* group per 1 g of specimen is less than $10^{9.3}$ cells, it can be determined that the subject is highly likely to have schizophrenia.

10. *Clostridium leptum* subgroup (1) Depression

The number of cells of *Clostridium leptum* subgroup in a depression patient is significantly smaller than that in a healthy subject. Specifically, when the number of cells of *Clostridium leptum* subgroup per 1 g of specimen is less than $10^{9.8}$ cells, it can be determined that the subject is highly likely to have depression.

(2) Manic depression

The number of cells of *Clostridium leptum* subgroup in a manic depression patient is significantly smaller than that in a healthy subject. Specifically, when the number of cells of *Clostridium leptum* subgroup per 1 g of specimen is less than $10^{10.2}$ cells, it can be determined that the subject is highly likely to have manic depression.

(3) Schizophrenia

The number of cells of *Clostridium leptum* subgroup in a schizophrenia patient is significantly smaller than that in a healthy subject. Specifically, when the number of cells of *Clostridium leptum* subgroup per 1 g of specimen is less than $10^{9.5}$ cells, it can be determined that the subject is highly likely to have schizophrenia.

11. *Staphylococcus*

(1) Manic Depression

The number of cells of *Staphylococcus* in a manic depression patient is significantly smaller than that in a healthy subject. Specifically, when the number of cells of *Staphylococcus* per 1 g of specimen is less than $10^{4.4}$ cells, it can be determined that the subject is highly likely to have manic depression.

12. *Clostridium Perfringens*

(1) Depression

The number of cells of *Clostridium perfringens* in a depression patient is significantly smaller than that in a healthy subject. Specifically, when the number of cells of *Clostridium perfringens* per 1 g of specimen is less than $10^{2.3}$ cells, it can be determined that the subject is highly likely to have depression.

(2) Manic Depression

The number of cells of *Clostridium perfringens* in a manic depression patient is significantly smaller than that in a healthy subject. Specifically, when the number of cells of *Clostridium perfringens* per 1 g of specimen is less than $10^{4.0}$ cells, it can be determined that the subject is highly likely to have manic depression.

(3) Schizophrenia

The number of cells of *Clostridium perfringens* in a schizophrenia patient is significantly smaller than that in a healthy subject. Specifically, when the number of cells of *Clostridium perfringens* per 1 g of specimen is less than $10^{4.7}$ cells, it can be determined that the subject is highly likely to have schizophrenia.

13. *Enterobacteriaceae*

(1) Depression

The number of cells of *Enterobacteriaceae* in a depression patient is significantly smaller than that in a healthy subject. Specifically, when the number of cells of *Enterobacteriaceae* per 1 g of specimen is less than $10^{6.4}$ cells, it can be determined that the subject is highly likely to have depression.

(2) Manic Depression

The number of cells of *Enterobacteriaceae* in a manic depression patient is significantly smaller than that in a healthy subject. Specifically, when the number of cells of *Enterobacteriaceae* per 1 g of specimen is less than $10^{7.2}$ cells, it can be determined that the subject is highly likely to have manic depression.

(3) Schizophrenia

The number of cells of *Enterobacteriaceae* in a schizophrenia patient is significantly smaller than that in a healthy subject. Specifically, when the number of cells of *Enterobacteriaceae* per 1 g of specimen is less than $10^{6.4}$ cells, it can be determined that the subject is highly likely to have schizophrenia.

14. Relationship between Enterobacteria and IBS in Manic Depression Patients

In terms of the number of cells of *Atopobium* cluster, *Clostridium coccoides* group, or *Staphylococcus*, manic depression patients having IBS were compared with manic depression patient not having IBS. As a result, the number of enterobacterial cells of each strain was significantly smaller in the patients having IBS than that in the patients not having IBS. Specifically, when the number of cells of *Atopobium* cluster per 1 g of specimen is less than $10^{8.9}$ cells, when the number of cells of *Clostridium coccoides* group per 1 g of specimen is less than $10^{9.3}$ cells, or when the number of cells of *Staphylococcus* per 1 g of specimen is less than $10^{3.5}$ cells, it can be determined that the manic depression patient is highly likely to have IBS.

In order to determine a mental disease (hereinafter the term "mental disease" includes mental diseases and IBS in patients with manic depression) by using the marker of the present invention, the number of the above described enterobacterial cells in a specimen may be measured. Examples of the specimen include biological samples derived from subjects, such as intestinal fluids or gastrointestinal contents such as feces. Among others, feces are particularly preferable because they impose less burden on subjects.

The measurement of enterobacteria in a specimen includes both determination of the presence or absence of enterobacteria (qualitative determination), and measurement of the number of enterobacterial cells (quantitative determination). Examples of the means for determining the presence or absence of enterobacteria include a culture method including culturing enterobacteria in a previously predicted selective medium and then confirming the presence or absence of colonies of target enterobacteria, a Southern hybridization method of detecting a target gene or mRNA derived from the target gene, a Northern hybridization method, and a DNA microarray method.

Examples of the means for measuring the number of enterobacterial cells in a specimen include a method including culturing enterobacteria in a previously predicted selective medium and then counting the number of cells, a method including culturing enterobacteria in a selective liquid medium and then measuring turbidity or absorbance, a FISH method, a real-time PCR method, and an RT-PCR method. Among these methods, an RT-PCR method is preferably applied.

Hereafter, the RT-PCR method will be described. An analysis method involving the RT-PCR method can be carried out, for example, by performing (1) a step of extracting RNA from enterobacteria of interest contained in a specimen, (2) a step of performing RT-PCR, using a nucleic acid fragment (primer) hybridizing to the extracted RNA, and (3) a step of detecting a DNA fragment amplified by the step (2). The above described nucleic acid fragment is combined with template cDNA derived from the specimen, and an amplification reaction is then carried out, so that a DNA fragment (PCR product) specific to the enterobacteria of interest can be obtained. The PCR product is observed over time, and the number of PCR cycles at which the PCR product reaches a predetermined amount of DNA, is then specified, so that it becomes possible to quantify the number of enterobacterial cells of interest in the specimen.

The observation of the amplified PCR product over time can be carried out by labeling the PCR product with an intercalating fluorescent dye such as SYBR(R) Green I, and then measuring the fluorescence intensity at each PCR stage. Since the intercalating dye has the property of intercalating in a double-stranded nucleic acid so as to increase the fluorescence intensity thereof, a PCR product generated from the cDNA of the target bacteria as a result of the PCR reaction can be accurately measured using such intercalating dye, and among others, SYBR(R) Green I is particularly preferably used.

By specifying the number of PCR cycles (hereinafter referred to as a $C_T$ value) at which the PCR product reaches an arbitrarily determined certain fluorescence intensity (DNA amount), it becomes possible to quantify the enterobacteria of interest contained in a specimen. In addition, TaqMan probe, Molecular Beacon, and the like, which are labeled with a fluorescent dye, can also be used. Such TaqMan probe or Molecular Beacon is a probe prepared by allowing a fluorescent dye and a quencher to bind to an oligonucleotide having homology with the internal sequence of a region amplified by PCR, and such TaqMan probe or Molecular Beacon is used by allowing them to coexist in the PCR reaction. Since fluorescence is emitted depending on the PCR amplification reaction by the interaction between a fluorescent dye and a quencher, which bind to a probe, the amplified PCR product can be observed over time by measuring the fluorescence intensity at each PCR stage.

The enterobacteria of interest contained in a specimen can be quantified by using a calibration curve obtained from the logarithmic value of the number of cells measured by a DAPI counting method, a culture method, etc., and a $C_T$ value. That is to say, a calibration curve is prepared in advance by plotting the logarithmic value of the number of cells of the target bacteria on the horizontal axis and plotting the $C_T$ value on the longitudinal axis, and the $C_T$ value obtained as a result of the PCR reaction is then applied to the calibration curve, so that the enterobacteria of interest in the specimen are quantified.

The presence or absence of a mental disease may be determined by using, as a criterion, the number of enterobacterial cells in a specimen derived from a healthy subject (in determination of the presence or absence of IBS in a manic depression patient, the number of cells of *Atopobium* cluster in a specimen derived from a manic depression patient not having IBS is used as a criterion). On the other hand, in determination of the severity of a mental disease, it can be determined that the smaller the number of enterobacterial cells, more severe the mental disease. It is preferable, however, that a criterion be determined in advance depending on the stage of severity.

In determination of the presence or absence of a mental disease, when one or more of the following criteria are satisfied, it can be determined that the subject is highly likely to have the following mental diseases (1) to (3). These criteria can also be used in combination.

(1) Depression (a) The number of cells of *Atopobium* cluster per 1 g of specimen is less than $10^{9.5}$ cells.

(b) The number of cells of *Lactobacillus* per 1 g of specimen is less than $10^{6.5}$ cells.
(c) The number of cells of *Lactobacillus brevis* per 1 g of specimen is less than $10^{3.7}$ cells.
(d) The number of cells of *Lactobacillus reuteri* subgroup per 1 g of specimen is less than $10^{4.7}$ cells.
(e) The number of cells of *Bifidobacterium* per 1 g of specimen is less than $10^{10.1}$ cells.
(f) The number of cells of *Enterococcus* per 1 g of specimen is less than $10^{7.1}$ cells.
(g) The number of cells of *Clostridium coccoides* group per 1 g of specimen is $10^{10.3}$ cells or more
(h) The number of cells of *Clostridium leptum* subgroup per 1 g of specimen is less than $10^{9.8}$ cells.
(i) The number of cells of *Clostridium perfringens* per 1 g of specimen is less than $10^{2.3}$ cells.
(j) The number of cells of *Enterobacteriaceae* per 1 g of specimen is less than $10^{6.4}$ cells.

(1) Manic Depression
(a) The number of cells of *Lactobacillus brevis* per 1 g of specimen is less than $10^{4.0}$ cells.
(b) The number of cells of *Lactobacillus reuteri* subgroup per 1 g of specimen is less than $10^{4.8}$ cells.
(c) The number of cells of *Enterococcus* per 1 g of specimen is $10^{5.0}$ cells or more
(d) The number of cells of *Clostridium coccoides* group per 1 g of specimen is less than $10^{9.3}$ cells.
(e) The number of cells of *Clostridium leptum* subgroup per 1 g of specimen is less than $10^{10.2}$ cells.
(f) The number of cells of *Staphylococcus* per 1 g of specimen is less than $10^{4.4}$ cells.
(g) The number of cells of *Clostridium perfringens* per 1 g of specimen is less than $10^{4.0}$ cells.
(h) The number of cells of *Enterobacteriaceae* per 1 g of specimen is less than $10^{7.2}$ cells.

(3) Schizophrenia
(a) The number of cells of *Atopobium* cluster per 1 g of specimen is less than $10^{9.5}$ cells.
(b) The number of cells of *Lactobacillus brevis* per 1 g of specimen is less than $10^{4.0}$ cells.
(c) The number of cells of *Lactobacillus reuteri* subgroup per 1 g of specimen is less than $10^{4.8}$ cells.
(d) The number of cells of *Lactobacillus sakei* subgroup per 1 g of specimen is less than $10^{4.8}$ cells.
(e) The number of cells of *Bacteroides fragilis* group per 1 g of specimen is less than $10^{6.1}$ cells.
(f) The number of cells of *Clostridium coccoides* group per 1 g of specimen is less than $10^{9.3}$ cells.
(g) The number of cells of *Clostridium leptum* subgroup per 1 g of specimen is less than $10^{9.5}$ cells.
(h) The number of cells of *Clostridium perfringens* per 1 g of specimen is less than $10^{4.7}$ cells.
(i) The number of cells of *Enterobacteriaceae* per 1 g of specimen is less than $10^{6.4}$ cells.

(4) IBS in Manic Depression
(a) The number of cells of *Atopobium* cluster per 1 g of specimen is less than $10^{8.8}$ cells.
(b) The number of cells of *Clostridium coccoides* group per 1 g of specimen is less than $10^{9.3}$ cells.
(c) The number of cells of *Staphylococcus* per 1 g of specimen is less than $10^{3.5}$ cells.

In determination of the severity of a mental disease, when one or more of the following criteria are satisfied, the severity of the following mental diseases (1) and (2) can be determined. These criteria can also be used in combination.

(1) Depression
(a) It is determined that when the number of cells of *Lactobacillus* per 1 g of specimen is $10^{6.5}$ cells or more, the anxiety symptom is highly likely to be at a mild degree, when it is $10^{6.4}$ to $10^{5.8}$ cells, the anxiety symptom is highly likely to be at a moderate degree, and when it is $10^{5.7}$ cells or less, the anxiety symptom is highly likely to be at a severe degree.

(2) Manic Depression
(a) Regarding obsessive symptom, it is determined that when the number of cells of *Bifidobacterium* per 1 g of specimen is $10^{9.9}$ cells or more, the obsessive symptom is highly likely to be at a mild degree, when it is $10^{9.8}$ to $10^{9.5}$ cells, the obsessive symptom is highly likely to be at a moderate degree, and when it is $10^{9.4}$ cells or less, the obsessive symptom is highly likely to be at a severe degree.
(b) Regarding interpersonal hypersensitivity, it is determined that when the number of cells of *Bifidobacterium* per 1 g of specimen is $10^{10.1}$ cells or more, the interpersonal hypersensitivity is highly likely to be at a mild degree, when it is $10^{10.0}$ to $10^{9.9}$ cells, the interpersonal hypersensitivity is highly likely to be at a moderate degree, and when it is $10^{9.8}$ cells or less, the interpersonal hypersensitivity is highly likely to be at a severe degree.
(c) Regarding anxiety symptom, it is determined that when the number of cells of *Bifidobacterium* per 1 g of specimen is $10^{9.7}$ cells or more, the anxiety symptom is highly likely to be at a mild degree, when it is $10^{9.6}$ to $10^{9.3}$ cells, the anxiety symptom is highly likely to be at a moderate degree, and when it is $10^{9.2}$ cells or less, the anxiety symptom is highly likely to be at a severe degree.
(d) Regarding depressive symptom, it is determined that when the number of cells of *Bifidobacterium* per 1 g of specimen is $10^{9.9}$ cells or more, the depressive symptom is highly likely to be at a mild degree, when it is $10^{9.9}$ to $10^{9.4}$ cells, the depressive symptom is highly likely to be at a moderate degree, and when it is $10^{9.3}$ cells or less, the depressive symptom is highly likely to be at a severe degree.

Moreover, in determination of the severity of a mental disease, when the number of the above described enterobacterial cells in a subject is continuously measured, if the number of enterobacterial cells tends to increase, the mental disease is determined to have become mild. In contrary, if the number of enterobacterial cells tends to decrease, the mental disease is determined to have become severe.

In order to carry out the method of determining a mental disease of the present invention, and in particular, the method of determining the presence or absence of a mental disease and/or the severity of such a mental disease, and the method of determining the presence or absence of IBS in a manic depression patient and/or the severity of such IBS, it is preferable to use a kit comprising protocols for measuring the above described enterobacteria contained in a specimen. The kit comprises a reagent for measuring the marker of the present invention and protocols (in which a method of measuring enterobacteria, and a method of determining a mental disease, and in particular, criteria for determining the presence or absence of a mental disease and/or the severity of such a mental disease, and the presence or absence of IBS in a manic depression patient and/or the severity of such IBS, factors which influence the measurement results, the degree of such influence, etc. are described). The determination criteria include the standard number of the above described enterobacterial cells, the number of cells, which is determined to be highly likely to have a mental disease, etc. Regarding determination of severity, the criteria include the predetermined range of the number of cells, which has been determined in advance depending on the stage of severity, etc. The aforementioned number of cells in the determination criteria can be determined for each target specimen and each type of mental symptom. Using the aforementioned criteria, determination can be carried out, as with the above described determination method. Herein, examples of the reagent for measuring the marker include a reagent for measuring the number of the aforementioned enterobacterial cells, a reagent for detecting mRNA, and a reagent for detecting DNA.

If a variation in the number of enterobacterial cells is employed as an index, a mental symptom-improving agent can be selected through screening. Herein, a "variation in the number of cells," which is used as an index, is a concept including a case where the number of enterobacterial cells has increased (risen) after administration of a test substance, a case where an increase (rising) in the number of enterobacterial cells is promoted when the number of cells is compared between before and after administration of a test substance, and a case where a decrease in the number of enterobacterial cells is suppressed when the number of cells is compared between before and after administration of a test substance. That is, a test substance, which has increased (raised) the number of enterobacterial cells, or has promoted an increase in the number of cells, or has suppressed a decrease in the number of cells in vitro or in vivo, is determined to have an action to improve mental symptoms.

For example, a test substance is administered to an experimental animal such as a human, a mouse, a rat, or a rabbit, and the administered animal is compared with an unadministered human or experimental animal. Then, whether or not the test substance changes the number of enterobacterial cells in a specimen is determined. When it is determined that the test substance has increased (raised) the number of enterobacterial cells, or has promoted an increase in the number of cells, or has suppressed a decrease in the number of cells, the test substance can be utilized as a mental symptom-improving agent.

EXAMPLES

Hereinafter, the present invention will be described in detail in the following examples.

[1] Used Strains

The strains shown in Table 1, which had been preserved at Yakult Central Institute, Yakult Honsha Co., Ltd., were used. The initial number of cells of each strain was adjusted to be approximately $1 \times 10^4$ cells.

The culture conditions of each strain are shown in Table 1. Details of culture conditions A to C are as follows.

Condition A: The strain was subjected to a static culture in a modified GAM broth with 1% glucose added at 37° C. under anaerobic conditions for 24 to 72 hours.

Condition B: The strain was subjected to a static culture in an MRS broth at 37° C. under anaerobic conditions for 24 to 72 hours.

Condition C: The strain was subjected to a shaking culture in a brain heart infusion broth at 37° C. under aerobic conditions for 18 hours.

These strains were measured in terms of the number of cells by a DAPI method, and were then diluted, as appropriate, to contain a predetermined number of cells, so that strain solutions were prepared.

TABLE 1

| Taxon | Strain | Culture condition |
|---|---|---|
| Atopobium cluster | Collinsella aerofaciens DSM 3979$^T$ | Condition A |
| Lactobacillus | Lactobacillus casei ATCC 334$^T$ | Condition B |
|  | Lactobacillus acidophilus ATCC 4356$^T$ |  |
|  | Lactobacillus plantarum ATCC 14917$^T$ |  |
|  | Lactobacillus reuteri JCM 1112$^T$ |  |
|  | Lactobacillus ruminis JCM 1152$^T$ |  |
|  | Lactobacillus sakei JCM 1157T |  |
|  | Lactobacillus brevis ATCC 14869$^T$ |  |
|  | Lactobacillus fermentum ATCC 14931$^T$ |  |
|  | Lactobacillus fructivorans JCM 1117$^T$ |  |
| Bifidobacterium | Bifidobacterium adolescentis ATCC 15703$^T$ | Condition A |
| Bacteroides fragilis group | Bacteroides vulgatus ATCC 8482$^T$ | Condition A |
| Enterococcus | Enterococcus faecalis ATCC 19433$^T$ | Condition B |
| Clostridium coccoides group | Blautia producta JCM 1471$^T$ | Condition A |
| Clostridium leptum subgroup | Faecalibacterium prausnitzii ATCC 27768$^T$ | Condition A |
| Staphylococcus | Staphylococcus aureus GIFU 9120$^T$ | Condition C |
| Clostridium perfringens | Clostridium perfringens JCM 1290$^T$ | Condition A |
| Enterobacteriaceae | Escherichia coli JCM 1649$^T$ | Condition C |

Reference Example 1

Preparation of specific primers for *Atopobium* cluster, *Lactobacillus*, *Lactobacillus brevis*, *Lactobacillus reuteri* subgroup, *Lactobacillus sakei* subgroup, *Bifidobacterium*, *Bacteroides fragilis* group, *Enterococcus*, *Clostridium coccoides* group, *Clostridium leptum* subgroup, *Staphylococcus*, *Clostridium perfringens* and *Enterobacteriaceae*

Primers used to measure the number of cells of the above described enterobacteria are shown in Table 2. In addition, publications, in which individual primers are described, are also shown in Table 2.

TABLE 2

| Target gene | Primer name | Sequence (5' - 3') | SEQ ID NO: | Publication |
|---|---|---|---|---|
| *Atopobium* cluster | c-Atopo-F | GGGTTGAGAGACCGACC | 1 | A |
|  | c-Atopo-R | CGGRGCTTCTTCTGCAGG | 2 | A |
| *Lactobacillus* | sg-Lcas-F | ACCGCATGGTTCTTGGC |  |  |
|  | sg-Lcas-R | CCGACAACAGTTACTCTGCC | 4 | B |
|  | sg-Lgas-F | GATGCATAGCCGAGTTGAGAGACTGAT | 5 | B |
|  | sg-Lgas-R | TAAAGGCCAGTTACTACCTCTATCC | 6 | B |
|  | sg-Lpla-F | CTCTGGTATTGATTGGTGCTTGCAT | 7 | B |
|  | sg-Lpla-R | GTTCGCCACTCACTCAAATGTAAA | 8 | B |
|  | sg-Lreu-F | GAACGCAYTGGCCCAA | 9 | B |
|  | sg-Lreu-R | TCCATTGTGGCCGATCAGT | 10 | B |
|  | sg-Lrum-F | CACCGAATGCTTGCAYTCACC | 11 | B |
|  | sg-Lrum-R | GCCGCGGGTCCATCCAAAA | 12 | B |
|  | sg-Lsak-F | CATAAAACCTAMCACCGCATGG | 13 | B |
|  | sg-Lsak-R | TCAGGTTACTATCAGATACRTTCTTCTC | 14 | B |
|  | s-Lbre-F | ATTTTGTTTGAAAGGTGGCTTCGG | 15 | C |
|  | s-Lbre-R | ACCCTTGAACAGTTACTCTCAAAGG | 16 | C |
|  | LFer-1 | CCTGATTGATTTTGGTCGCCAAC | 17 | B |
|  | LFer-2 | ACGTATGAACAGTTACTCTCATACGT | 18 | B |
|  | s-Lfru-F | TGCGCCTAATGATAGTTGA | 19 | B |
|  | s-Lfru-R | GATACCGTCGCGACGTGAG | 20 | B |
| *Bifidobacterium* | g-Bifid-F | CTCCTGGAAACGGGTGG | 21 | D |
|  | g-Bifid-R | GGTGTTCTTCCCGATATCTACA | 22 | D |
| *Bacteroides fragilis* group | g-Bfra-F2 | AYAGCCTTTCGAAAGRAAGAT | 23 | G |
|  | g-Bfra-R | CCAGTATCAACTGCAATTTTA | 24 | E |
| *Enterococcus* | g-Encoc-F | ATCAGAGGGGGATAACACTT | 25 | B |
|  | g-Encoc-R | ACTCTCATCCTTGTTCTTCTC | 26 | B |
| *Clostridium coccoides* group | g-Ccoc-F | AAATGACGGTACCTGACTAA | 27 | E |
|  | g-Ccoc-R | CTTTGAGTTTCATTCTTGCGAA | 28 | E |
| *Clostridium leptum* subgroup | sg-Clept-F | GCACAAGCAGTGGAGT | 29 | F |
|  | sg-Clept-R | CTTCCTCCGTTTTGTCAA | 30 | F |
| *Staphylococcus* | g-Staph-F | TTTGGGCTACACACGTGCTACAATGGACAA | 31 | B |
|  | g-Staph-R | AACAACTTTATGGGATTTGCWTGA | 32 | B |
| *Clostridium perfringens* | s-Clper-F | GGGGGTTTCAACACCTCC | 33 | B |
|  | ClPER-R | GCAAGGGATGTCAAGTGT | 34 | H |

TABLE 2-continued

| Target gene | Primer name | Sequence (5' - 3') | SEQ ID NO: | Publication |
|---|---|---|---|---|
| *Enterobacteriaceae* | f-Enbac-F | TGCCGTAACTTCGGGAGAAGGCA | 35 | B |
| | f-Enbac-R | TCAAGGACCAGTGTTCAGTGTC | 36 | B |

A: Matsuki T, Watanabe K, Fujimoto J, et al. Quantitative PCR with 16S rRNA-gene-targeted species-specific primers for analysis of human intestinal *bifidobacteria*. Applied and Environmental Microbiology 2004; 70: 167-73.
B: Matsuda K., Tsuji H., Asahara T., Matsumoto K., Takada T., and Nomoto K. Establishment of an Analytical System for the Human Fecal Microbiota, Based on Reverse Transcription-Quantitative PCR Targeting of Multicopy rRNA Molecules. Appl Environ Microbiol 2009; 75: 1961-1969.
C: JP-A-2001-112485
D: Matsuki T, Watanabe K, Tanaka R, et al. Rapid identification of human intestinal *bifidobacteria* by 16S rRNA-targeted species- and group-specific primers. FEMS Microbiol Lett 1998; 167: 113-21.
E: Matsuki T, Watanabe K, Fujimoto J, et al. Development of 16S rRNA-gene-targeted group-specific primers for the detection and identification of predominant bacteria in human feces. Appl Environ Microbiol 2002; 68: 5445-51.
F: Matsuki T, Watanabe K, Fujimoto J, et al. Use of 16S rRNA gene-targeted group-specific primers for real-time PCR analysis of predominant bacteria in human feces. Appl Environ Microbiol 2004; 70: 7220-8.
G: Matsuki, T. Development of quantitative PCR detection method with 16S rRNA gene-targeted genus- and species- specific primers for the analysis of human intestinal microflora and its application. Nippon Saikingaku Zasshi 2007; 62: 255-261.
H: Kikuchi E., Miyamoto Y., Narushima S., and Itoh K. Design of species-specific primers to identify 13 species of *Clostridium* harbored in human intestinal tracts. Microbiol Immunol 2002; 46: 353-358.

Reference Example 2

Preparation of calibration curve used in RT-PCR

A calibration curve, which was to be used upon quantification of the desired enterobacteria in a specimen, was produced. Specifically, according to the following procedures, a calibration curve was prepared by plotting the number of enterobacterial cells counted by a DAPI counting method on the horizontal axis and plotting the $C_T$ value on the longitudinal axis.

1) 400 µL of RNAlater (Ambion) was added to 200 µL of each strain solution prepared in the above "[1] Used strains," and the mixed solution was then left to stand at a room temperature for 5 minutes. Thereafter, the reaction mixture was centrifuged at 13,000 g for 5 minutes, and a supernatant was then removed by decantation. Subsequently, 450 µL of a lysis buffer (which was prepared by mixing 346.5 µL of an RLT buffer, 100 µL of TE and 3.5 µL of β-Mercaptoethanol, for a single sample) and 300 mg of glass beads having a diameter of 0.1 mm (TOMY SEIKO CO., LTD.) were added to the residue from which the supernatant had been removed.

2) A sample tube was set into a shaker (ShakeMaster), and was then shaken for 5 minutes, so that the cells were disintegrated.

3) 500 µL of water-saturated phenol was added to the resulting cells, and the obtained mixture was then stirred by vortexing for 5 to 10 seconds.

4) The sample tube was set into a heat block at 60° C., and the reaction was then carried out for 10 minutes (hot phenol method).

5) 100 µL of Chloroform/Isoamyl alcohol (24:1) was added to the reaction product, and the obtained mixture was then stirred by vortexing 5 to 10 seconds.

6) After completion of centrifugation (13,000 g×5 min), 470 µL of a supernatant was transferred into a new microtube with a lid (1.5 mL).

7) 470 µL of Chloroform/Isoamyl alcohol (24:1) was added to the supernatant, and the obtained mixture was then stirred by vortexing for 5 to 10 seconds.

8) After completion of centrifugation (13,000 g×5 min), 400 µL of a supernatant was then transferred into a new microtube with a lid (1.5 mL).

9) 40 µL of 3 M sodium acetate (pH 5.4) and 400 µL of Isopropanol were added to the supernatant, and they were then subjected to inversion mixing.

10) The resulting mixture was subjected to centrifugation (20,000 g×10 min).

11) A supernatant was removed by decantation, and 500 µL of 80% Ethanol was then added to the residue.

12) After completion of centrifugation (20,000 g×2 min), a supernatant was removed by decantation.

13) After completion of air-drying (the opening was directed upwards, for approximately 20 minutes), Nuclease-free water (Ambion) was added to the resultant, such that the cell density could be $2 \times 10^8$ cells/mL based on the cell number measurement according to the DAPI method, and the mixed solution was stirred for uniform dissolution. Thereafter, using Nuclease-free water, 10-fold serial dilution was carried out, and diluted samples in the range of $2 \times 10^{-3}$ to $2 \times 10$ cells/mL were each used as RNA samples described in 14) below. Such an RNA sample was subjected to an RT-qPCR reaction.

14) RT-qPCR was carried out using QIAGEN OneStep RT-PCR Kit (QIAGEN). With regard to the composition of a reaction solution, a reaction solution (total amount: 10 µL) containing 1×QIAGEN OneStep RT-PCR Buffer, 0.5×Q-Solution, 0.4 mM dNTP Mix, QIAGEN OneStep RT-PCR Enzyme Mix (in an amount of 1/25), SYBR(R) Green I (Molecular Probes) (in an amount of 1/100,000), 1×ROX Reference Dye (Invitrogen), 0.60 µM each primer shown in Table 2, and 5 µL of the RNA sample prepared in the above 13) was used in the reaction.

15) The reaction solution was first subjected to a reverse transcription reaction at 50° C. for 30 minutes, and thereafter, the obtained solution was heated at 95° C. for 15 minutes to inactivate reverse transcriptase. Subsequently, a cycle consisting of 94° C. for 20 seconds, 55° C. or 60° C. (wherein 55° C. was applied to SEQ ID NOS: 1, 2, and 15 to 28 of Table 2, and 60° C. was applied to SEQ ID NOS: 3 to 14, 29, and 30 of Table 2) for 20 seconds, and 72° C. for 50 seconds was carried out 45 times, so as to obtain an amplification product. The amount of the amplification product was measured in terms of the fluorescence intensity of SYBR(R) Green I for each cycle, and a PCR curve was produced. The baseline and threshold of fluorescence intensity were determined, and the number of cycles in which the PCR curve intersects with the threshold (Threshold cycle: $C_T$ value) was obtained. The obtained $C_T$ value was plotted on the longitudinal axis, and the number of cells in the sample subjected to the PCR reaction was plotted on the horizontal axis. For these analyses, Sequence Detection System (SDS) software (Applied Biosystems) was used. In order to confirm whether or not the PCR amplification was specifically carried out, a denaturation temperature was measured, separately. The denaturation temperature was measured by reacting the above-obtained amplification product at 94° C. for 15 seconds, then slowly increasing the temperature from 55° C. or 60° C. up to 99° C. at a speed of 0.2° C./sec, then plotting the temperature on the x-axis and plotting the fluorescence intensity of SYBR(R) Green I on the y-axis to produce a denaturation curve of the amplification product, and then measuring the temperature at which the fluorescence intensity sharply decreased. A series of these reactions were carried out using ABI PRISM(R) 7900HT System (Applied Biosystems).

16) The number of cells of the enterobacteria of each strain, which was measured by a DAPI method, was plotted on the x-axis, and the $C_T$ value obtained by RT-qPCR corresponding thereto was plotted on the y-axis, so as to produce a calibration curve.

Example 1

Relationship between Mental Disease and Enterobacterial Flora

The enterobacterial flora of a patient with a mental disease (depression, manic depression, or schizophrenia) was carefully investigated, and the relationship between such a mental disease and the enterobacterial flora was evaluated.

(1) Diagnosis of Mental Disease

A mental disease was diagnosed by a psychiatrist, using a mental disease mini-international neuropsychiatric interview MINI (Mini-International Neuropsychiatric Interview, Japanese edition: Otsubo T, et al. Reliability and validity of Japanese version of the Mini-International Neuropsychiatric Interview. Psychiatry and Neurosciences 2005; 59: 517-526.). Each patient was diagnosed healthy or with any one of depression, manic depression, and schizophrenia.

(2) Acquisition of Specimens

After completion of the diagnosis of the mental disease described in the above (1), feces obtained from the following patients were excluded from specimens.
(a) Males and females older than or equal to 63 years
(b) Patients with complications of severe medical diseases
(c) Patients taking antibiotics
(d) Patients having intellectual disability, epilepsy, or severe congenital abnormality
(e) Patients with surgical history of intestinal tract As a result of such elimination, the obtained specimens were feces collected from 62 healthy subjects (Normal), 43 depression patients (MDD), 39 manic depression patients (MDI), and 47 schizophrenia patients (Sz).

(3) Quantification of Enterobacterial Cells in Specimens
(a) Preparation of Samples for RNA Extraction 0.2 mL of RNAlater (Ambion) was added to 4 mg of a specimen, and the mixture was then left to stand at a room temperature for 5 minutes. Thereafter, the reaction mixture was centrifuged at 14,000 g for 10 minutes, and a supernatant was then removed by decantation. The residue was used as a sample for RNA extraction.

(b) Nucleic Acid Extraction

An RNA extraction operation was carried out according to the following procedures.

1) 450 μL of a lysis buffer (which was prepared by mixing 346.5 μL of an RLT buffer, 100 μL of TE and 3.5 μL of β-Mercaptoethanol, for a single sample) and 300 mg of glass beads having a diameter of 0.1 mm were added to the sample for RNA extraction prepared in the above (a).

2) A nucleic acid extraction operation was carried out in the same manner as the methods described in 2) to 12) of the above Reference Example 2.

3) After completion of air-drying (the opening was directed upwards, for approximately 20 minutes), 200 μL of Nuclease-free water was added to the resultant, and the mixed solution was then stirred for uniform dissolution, thereby preparing an RNA sample.

(c) Measurement of the Number of Cells

An RT-qPCR method was applied to the RNA sample obtained in the above (b) to measure the number of cells. RT-qPCR was carried out in the same manner as the methods described in 14) and 15) of the above Reference Example 2. It is to be noted that the number of cells of *Lactobacillus* was measured using the primers shown as the SEQ ID NOS: 3 to 20. The number of cells of *Lactobacillus* was obtained as a total sum of the number of cells of *Lactobacillus casei* subgroup, *Lactobacillus gasseri* subgroup, *Lactobacillus plantarum* subgroup, *Lactobacillus reuteri* subgroup, *Lactobacillus ruminis* subgroup, *Lactobacillus sakei* subgroup, *Lactobacillus brevis*, *Lactobacillus fermentum* and *Lactobacillus fructivorans*.

(4) Analysis Method
(a) Analysis regarding relationship between the presence or absence of mental disease and the number of enterobacterial cells 1) Comparison between Mental Disease Patients and Healthy Subjects in Terms of the Number of Cells An examination regarding a difference between the number of cells of each enterobacterial strain in depression, manic depression and schizophrenia patients, and the number of cells of each enterobacterial strain in healthy subjects was carried out according to a Mann-Whitney u-test. The analysis target number in the healthy subject group was adjusted, so that a statistical significance was not generated depending on the sex and age of each disease group.

2) Comparison using Cut-Off Value

Receiver Operating analysis (ROC) was carried out, and a cut-off value, which most efficiently identifies the number of cells of each enterobacterial strain in depression, manic depression and schizophrenia patients and in healthy subjects, was obtained. Then, the ratio of the number of people having the number of cells, which was less than the cut-off value, was calculated in depression, manic depression and schizophrenia patients and in healthy subjects.

(b) Analysis Regarding Relationship between the Severity of Mental Disease and the Number of Enterobacterial Cells 1) Evaluation of severity and the number of enterobacterial cells according to GRID HAM-D As a method of evaluating the severity of depression, GRID Hamilton Depression Rating Scale (GRID-HAND) (Hamilton, M., A rating scale of depression. J. Neural. Neurosurg. Psychiatry 1960; 23, 56-62. and A. Kalali, et al., The new GRID HAM-D: pilot testing and international field trials. International Journal of Neuropsychopharmacology. 2002; 5, S147-S148.) was used. In the present evaluation, among the GRID-HAND rating scales, HAMD21 composed of 21 questionnaires was used. A score of 0 to 7 was determined to be normal (remission), a score of 8 to 13 was determined to be a mild degree, a score of 14 to 18 was determined to be a moderate degree, and a score of 19 or greater was determined to be a severe degree.

2) Evaluation of severity and the number of enterobacterial cells according to HSCL, a self-report measure of stress Using the HSCL, a self-report measure of stress, (Derogatis L R, et al., The Hopkins Symptom Checklist (HSCL): a self-report symptom inventory. Behavioral science 1974; 19, 1-15. and Keiko Nakano 2005. Stress Management Nyumon, Jiko Sindan to Taishoho wo Manabu (Basic Stress Management, Studies of Self-Diagnosis and Approaches), Kongo Shuppan), the score of each of psychosomatic symptom, obsession, interpersonal hypersensitivity, anxiety symptom and depressive symptom, and the total score of these symptoms were calculated. Thereafter, an examination regarding a difference between the scores of depression and manic depression patients and the scores of healthy subjects was carried out according to a Mann-Whitney u-test.

(c) Analysis Regarding Relationship between the Presence or Absence of IBS in Manic Depression Patients, and the Number of Cells of *Atopobium* Cluster, *Clostridium Coccoides* Group, and *Staphylococcus*

For the diagnosis of IBS, Rome III diagnosis criteria (Longstreth GF, et al., Functional bowel disorders. Gastroenterology. 2006; 130, 1480-91), which was defined as an international standard, was used.

A manic depression group was divided into two groups, namely, a group having IBS and a group not having IBS, and an examination regarding a difference in terms of the number of cells of *Atopobium* cluster, *Clostridium coccoides* group, and *Staphylococcus*, between the group having IBS and the group not having IBS, was carried out according to a Mann-Whitney u-test.

(5) Results
(a) *Atopobium* Cluster
1) Depression

In the comparison using a cut-off value described in the above (4)(a)2), when the ratio of depression patients in which the number of cells of *Atopobium* cluster was less than $10^{9.5}$ cells was compared with the ratio of healthy subjects in which the number of cells of *Atopobium* cluster was less than $10^{9.5}$ cells, the ratio of depression patients was significantly higher than the ratio of healthy subjects, as shown in Table 3. Accordingly, it was found that when the number of cells of *Atopobium* cluster per 1 g of feces is less than $10^{9.5}$ cells, it can be determined that the subject is highly likely to have depression.

TABLE 3

| | Cut-off value* | Ratio of less than cut-off value | P value |
|---|---|---|---|
| Healthy subject n = 57 | 9.5 | 22/57 (39%) | P < 0.001 |
| Depression n = 43 | | 35/43 (81%) | |

*The number of cells per 1 g of feces (Log10 cells/g fecal) is indicated.

2) Schizophrenia

In the comparison with healthy subjects in terms of the number of cells described in the above (4)(a)1), the number of cells of *Atopobium* cluster was significantly smaller in schizophrenia patients than in healthy subjects, as shown in Table 4. In addition, in the comparison using a cut-off value described in the above (4)(a)2), when the ratio of schizophrenia patients in which the number of cells of *Atopobium* cluster was less than $10^{9.5}$ cells was compared with the ratio of healthy subjects in which the number of cells of *Atopobium* cluster was less than $10^{9.5}$ cells, the ratio of schizophrenia patients was significantly higher than the ratio of healthy subjects, as shown in Table 5. Accordingly, it was found that when the number of cells of *Atopobium* cluster per 1 g of feces is less than $10^{9.5}$ cells, it can be determined that the subject is highly likely to have schizophrenia.

TABLE 4

| | Median (minimum value-maximum value)* | P value |
|---|---|---|
| Healthy subject n = 51 | 9.6 (8.1-10.2) | P = 0.026 |
| Schizophrenia n = 47 | 9.3 (5.6-10.4) | |

*The number of cells per 1 g of feces (Log10 cells/g fecal) is indicated.

TABLE 5

| | Cut-off value* | Ratio of less than cut-off value | P value |
|---|---|---|---|
| Healthy subject n = 51 | 9.5 | 21/51 (41%) | P = 0.001 |
| Schizophrenia n = 47 | | 35/47 (74%) | |

*The number of cells per 1 g of feces (Log10 cells/g fecal) is indicated.

(b) *Lactobacillus*
1) Depression

In the comparison using a cut-off value described in the above (4)(a)2), when the ratio of depression patients in which the number of cells of *Lactobacillus* was less than $10^{6.5}$ cells was compared with the ratio of healthy subjects in which the number of cells of *Lactobacillus* was less than $10^{6.5}$ cells, the ratio of depression patients was significantly higher than the ratio of healthy subjects, as shown in Table 6. Accordingly, it was found that when the number of cells of *Lactobacillus* per 1 g of feces is less than $10^{6.5}$ cells, it can be determined that the subject is highly likely to have depression.

In addition, in the evaluation according to the self-report measure of stress HSCL described in (4)(b)2), a significant correlation was obtained in the case of depression patients, such that as the score of anxiety symptom has increased, the number of cells of *Lactobacillus* has decreased, and as the score has decreased, the number of cells has increased (FIG. 1). Specifically, regarding anxiety symptom, it was found that it can be determined that when the number of cells of *Lactobacillus* per 1 g of feces is $10^{6.5}$ cells or more, the anxiety symptom is highly likely to be at a mild degree, when it is $10^{6.4}$ to $10^{5.8}$ cells, the anxiety symptom is highly likely to be at a moderate degree, and when it is $10^{5.7}$ cells or less, the anxiety symptom is highly likely to be at a severe degree.

TABLE 6

| | Cut-off value* | Ratio of less than cut-off value | P value |
|---|---|---|---|
| Healthy subject n = 57 | 6.5 | 25/57 (44%) | P = 0.044 |
| Depression n = 43 | | 28/43 (65%) | |

*The number of cells per 1 g of feces (Log10 cells/g fecal) is indicated.

(c) *Lactobacillus Brevis*
1) Depression

In the comparison using a cut-off value described in the above (4)(a)2), when the ratio of depression patients in which the number of cells of *Lactobacillus brevis* was less than $10^{3.7}$ cells was compared with the ratio of healthy subjects in which the number of cells of *Lactobacillus brevis* was less than $10^{3.7}$ cells, the ratio of depression patients was significantly higher than the ratio of healthy subjects, as shown in Table 7. Accordingly, it was found that when the number of cells of *Lactobacillus brevis* per 1 g of feces is less than $10^{3.7}$ cells, it can be determined that the subject is highly likely to have depression.

TABLE 7

| | Cut-off value* | Ratio of less than cut-off value | P value |
|---|---|---|---|
| Healthy subject n = 57 | 3.7 | 47/57 (82%) | P = 0.022 |
| Depression n = 43 | | 42/43 (98%) | |

*The number of cells per 1 g of feces (Log10 cells/g fecal) is indicated.

2) Manic Depression

In the comparison using a cut-off value described in the above (4) (a)2), when the ratio of manic depression patients in which the number of cells of *Lactobacillus brevis* was less than $10^{4.0}$ cells was compared with the ratio of healthy subjects in which the number of cells of *Lactobacillus brevis* was less than $10^{4.0}$ cells, the ratio of manic depression patients was significantly higher than the ratio of healthy subjects, as shown in Table 8.

Accordingly, it was found that when the number of cells of *Lactobacillus brevis* per 1 g of feces is less than $10^{4.0}$ cells, it can be determined that the subject is highly likely to have manic depression.

TABLE 8

| | Cut-off value* | Ratio of less than cut-off value | P value |
|---|---|---|---|
| Healthy subject n = 58 | 4.0 | 49/58 (84%) | P = 0.046 |
| Manic depression n = 39 | | 38/39 (97%) | |

*The number of cells per 1 g of feces (Log10 cells/g fecal) is indicated.

3) Schizophrenia

In the comparison using a cut-off value described in the above (4)(a)2), when the ratio of schizophrenia patients in which the number of cells of *Lactobacillus brevis* was less than $10^{4.0}$ cells was compared with the ratio of healthy subjects in which the number of cells of *Lactobacillus brevis* was less than $10^{4.0}$ cells, the ratio of schizophrenia patients was significantly higher than the ratio of healthy subjects, as shown in Table 9. Accordingly, it was found that when the number of cells of *Lactobacillus brevis* per 1 g of feces is less than $10^{4.0}$ cells, it can be determined that the subject is highly likely to have schizophrenia.

TABLE 9

| | Cut-off value* | Ratio of less than cut-off value | P value |
|---|---|---|---|
| Healthy subject n = 51 | 4.0 | 41/51 (80%) | P = 0.021 |
| Schizophrenia n = 47 | | 45/47 (96%) | |

*The number of cells per 1 g of feces (Log10 cells/g fecal) is indicated.

(d) *Lactobacillus Reuteri* Subgroup

1) Depression

In the comparison using a cut-off value described in the above (4)(a)2), when the ratio of depression patients in which the number of cells of *Lactobacillus reuteri* subgroup was less than $10^{4.7}$ cells was compared with the ratio of healthy subjects in which the number of cells of *Lactobacillus reuteri* subgroup was less than $10^{4.7}$ cells, the ratio of depression patients was significantly higher than the ratio of healthy subjects, as shown in Table 10. Accordingly, it was found that when the number of cells of *Lactobacillus reuteri* subgroup per 1 g of feces is less than $10^{4.7}$ cells, it can be determined that the subject is highly likely to have depression.

TABLE 10

| | Cut-off value* | Ratio of less than cut-off value | P value |
|---|---|---|---|
| Healthy subject n = 57 | 4.7 | 20/57 (35%) | P = 0.001 |
| Depression n = 43 | | 30/43 (70%) | |

*The number of cells per 1 g of feces (Log10 cells/g fecal) is indicated.

2) Manic Depression

In the comparison using a cut-off value described in the above (4)(a)2), when the ratio of manic depression patients in which the number of cells of *Lactobacillus reuteri* subgroup was less than $10^{4.8}$ cells was compared with the ratio of healthy subjects in which the number of cells of *Lactobacillus reuteri* subgroup was less than $10^{4.8}$ cells, the ratio of manic depression patients was significantly higher than the ratio of healthy subjects, as shown in Table 11. Accordingly, it was found that when the number of cells of *Lactobacillus reuteri* subgroup per 1 g of feces is less than $10^{4.8}$ cells, it can be determined that the subject is highly likely to have manic depression.

TABLE 11

| | Cut-off value * | Ratio of less than cut-off value | P value |
|---|---|---|---|
| Healthy subject n = 58 | 4.8 | 20/58 (34%) | P = 0.038 |
| Manic depression n = 39 | | 22/39 (56%) | |

* The number of cells per 1 g of feces (Log10 cells/g fecal) is indicated.

3) Schizophrenia

In the comparison using a cut-off value described in the above (4) (a)2), when the ratio of schizophrenia patients in which the number of cells of *Lactobacillus reuteri* subgroup was less than $10^{4.8}$ cells was compared with the ratio of healthy subjects in which the number of cells of *Lactobacillus reuteri* subgroup was less than $10^{4.8}$ cells, the ratio of schizophrenia patients was significantly higher than the ratio of healthy subjects, as shown in Table 12. Accordingly, it was found that when the number of cells of *Lactobacillus reuteri* subgroup per 1 g of feces is less than $10^{4.8}$ cells, it can be determined that the subject is highly likely to have schizophrenia.

TABLE 12

| | Cut-off value * | Ratio of less than cut-off value | P value |
|---|---|---|---|
| Healthy subject n = 51 | 4.8 | 19/51 (37%) | P = 0.029 |
| Schizophrenia n = 47 | | 29/47 (62%) | |

* The number of cells per 1 g of feces (Log10 cells/g fecal) is indicated.

(e) *Lactobacillus Sakei* Subgroup

1) Schizophrenia

In the comparison using a cut-off value described in the above (4)(a)2), when the ratio of schizophrenia patients in which the number of cells of *Lactobacillus sakei* subgroup was less than $10^{4.8}$ cells was compared with the ratio of healthy subjects in which the number of cells of *Lactobacillus sakei* subgroup was less than $10^{4.8}$ cells, the ratio of schizophrenia patients was significantly higher than the ratio of healthy subjects, as shown in Table 13. Accordingly, it was found that when the number of cells of *Lactobacillus sakei* subgroup per 1 g of feces is less than $10^{4.8}$ cells, it can be determined that the subject is highly likely to have schizophrenia.

TABLE 13

|  | Cut-off value * | Ratio of less than cut-off value | P value |
| --- | --- | --- | --- |
| Healthy subject n = 51 | 4.8 | 33/51 (65%) | P = 0.011 |
| Schizophrenia n = 47 |  | 41/47 (87%) |  |

* The number of cells per 1 g of feces (Log10 cells/g fecal) is indicated.

(f) *Bifidobacterium*
1) Depression

In the comparison with healthy subjects in terms of the number of cells described in the above (4)(a)1), the number of cells of *Bifidobacterium* was significantly smaller in depression patients than in healthy subjects, as shown in Table 14. In addition, in the comparison using a cut-off value described in the above (4)(a)2), when the ratio of depression patients in which the number of cells of *Bifidobacterium* was less than $10^{10.1}$ cells was compared with the ratio of healthy subjects in which the number of cells of *Bifidobacterium* was less than $10^{10.1}$ cells, the ratio of depression patients was significantly higher than the ratio of healthy subjects, as shown in Table 15. Accordingly, it was found that when the number of cells of *Bifidobacterium* per 1 g of feces is less than $10^{10.1}$ cells, it can be determined that the subject is highly likely to have depression.

TABLE 14

|  | Median (minimum value-maximum value)* | P value |
| --- | --- | --- |
| Healthy subject n = 51 | 10.0 (2.5-10.9) | P = 0.012 |
| Depression n = 47 | 9.5 (5.4-11.3) |  |

*The number of cells per 1 g of feces (Log10 cells/g fecal) is indicated.

TABLE 15

|  | Cut-off value * | Ratio of less than cut-off value | P value |
| --- | --- | --- | --- |
| Healthy subject n = 57 | 10.1 | 32/57 (56%) | P = 0.005 |
| Depression n = 43 |  | 36/43 (84%) |  |

* The number of cells per 1 g of feces (Log10 cells/g fecal) is indicated.

Figure 2:
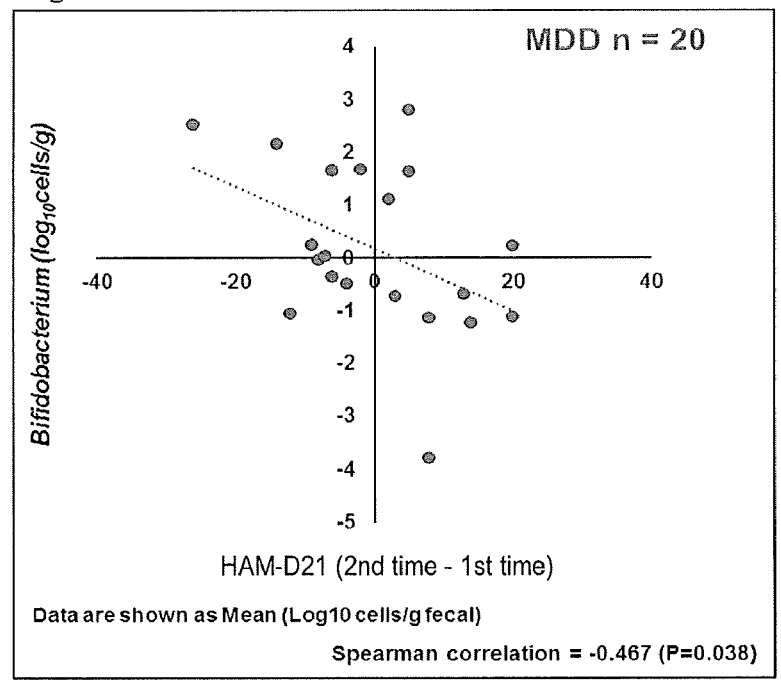
FIG. 2 shows a correlation between a difference in the HAM-D21 scores on the 0th month and on the 6th month, and a difference in the numbers of cells of *Bifidobacterium* on the 0th month and on the 6th month. In depression patients in which the number of cells on the 6th month has been increased in comparison to that on the 0th month, the HAM-D21 score has been decreased, and depressive symptom has been alleviated.
Figure 3:
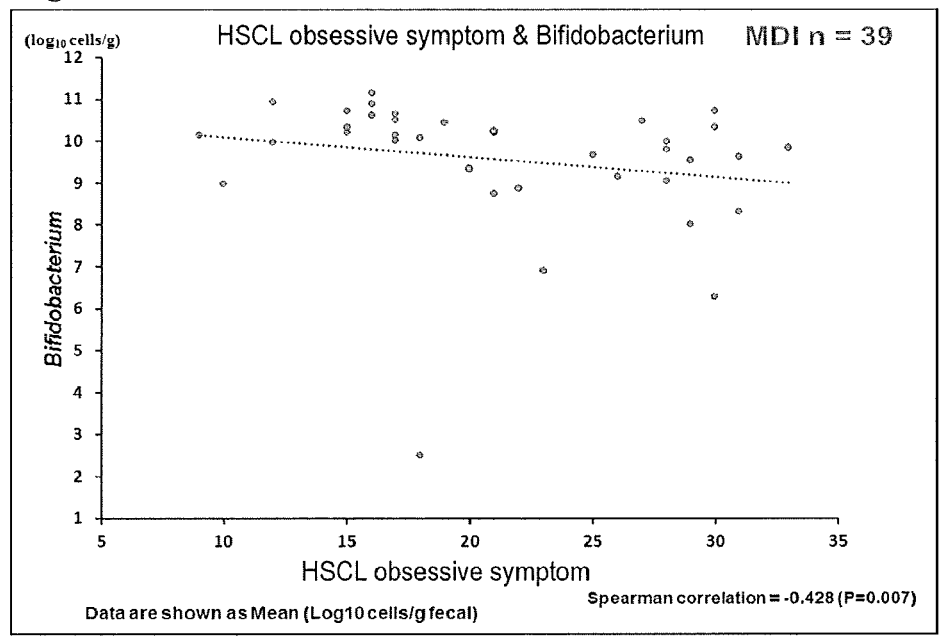
FIG. 3 shows a correlation between the number of cells of *Bifidobacterium* in manic depression patients and the score of obsessive symptom according to the HSCL, a self-report measure of stress. The higher the severity, the smaller the number of cells. In contrast, the lower the severity, the larger the number of cells.
Figure 4:
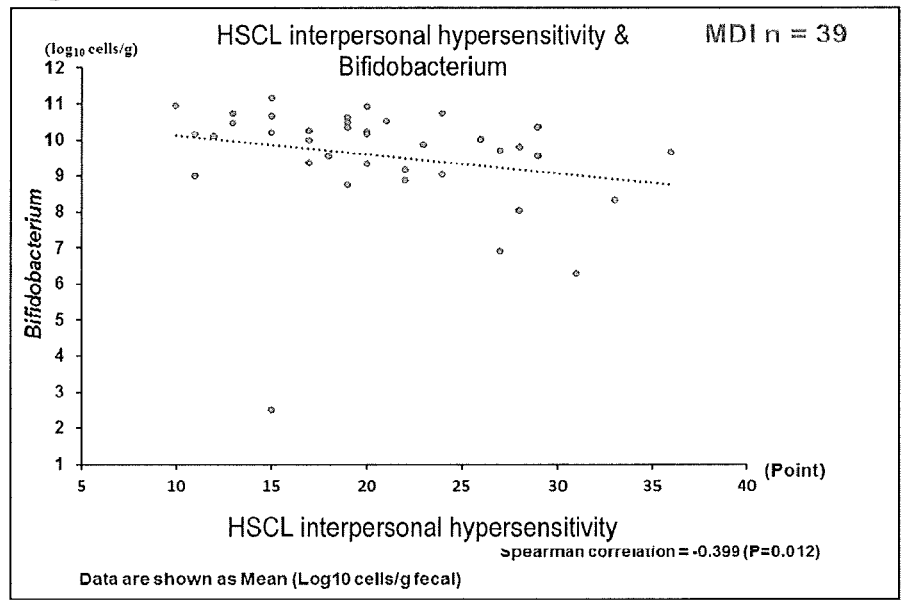
FIG. 4 shows a correlation between the number of cells of *Bifidobacterium* in manic depression patients and the score of interpersonal hypersensitivity according to the HSCL, a self-report measure of stress. The higher the score of interpersonal hypersensitivity, the smaller the number of cells. In contrast, the lower the score of interpersonal hypersensitivity, the larger the number of cells.
Figure 5:
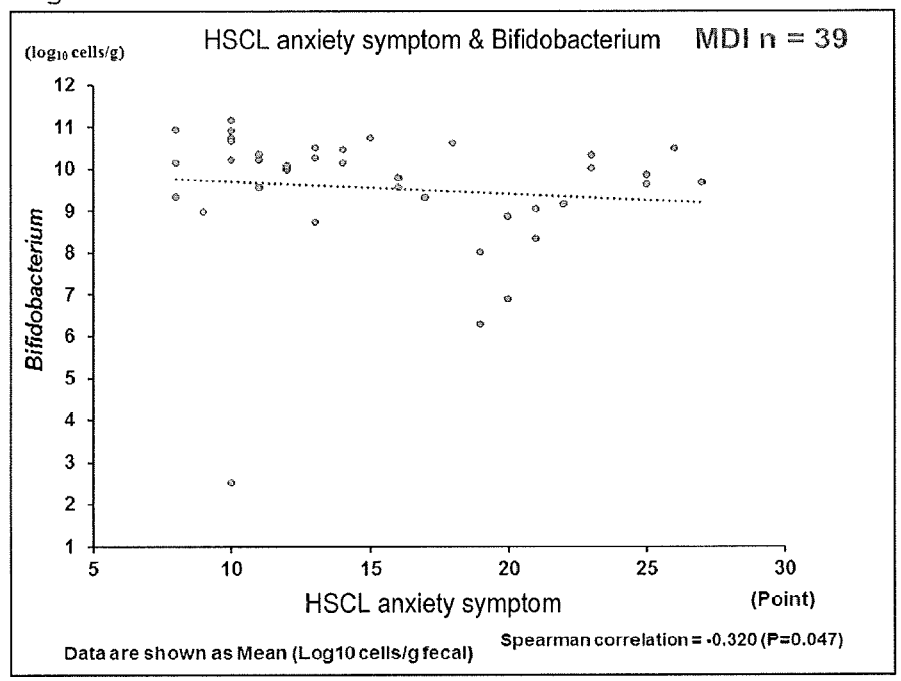
FIG. 5 shows a correlation between the number of cells of *Bifidobacterium* in manic depression patients and the score of anxiety symptom according to the HSCL, a self-report measure of stress. The higher the score of anxiety symptom, the smaller the number of cells. In contrast, the lower the score of anxiety symptom, the larger the number of cells.
Figure 6:
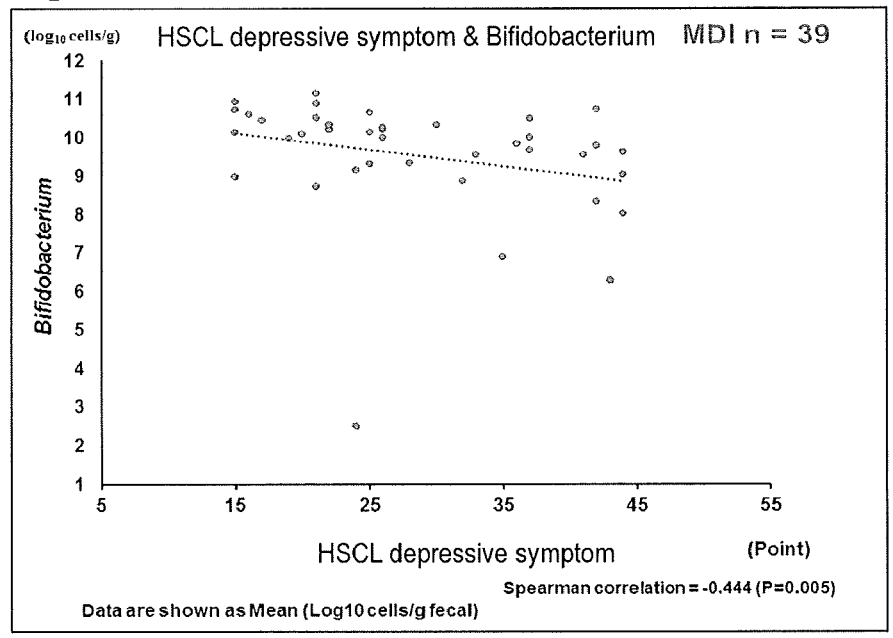
FIG. 6 shows a correlation between the number of cells of *Bifidobacterium* in manic depression patients and the score of depressive symptom according to the HSCL, a self-report measure of stress. The higher the score of depressive symptom, the smaller the number of cells. In contrast, the lower the score of depressive symptom, the larger the number of cells.
Figure 7:
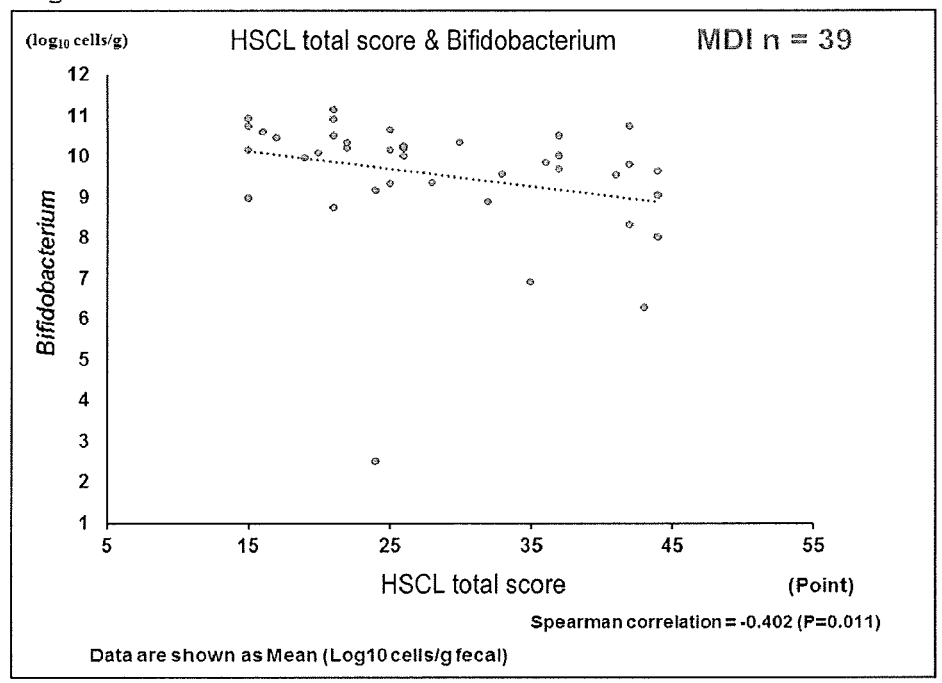
FIG. 7 shows a correlation between the number of cells of *Bifidobacterium* in manic depression patients and the total score obtained according to the HSCL, a self-report measure of stress. The higher the total score of HSCL, the smaller the number of cells. In contrast, the lower the total score of HSCL, the larger the number of cells.

Moreover, in the evaluation according to GRID HAM-D described in the above (4)(b)1), a difference between the HAM-D21 score on the 0th month and the HAM-D21 score on the 6th month in depression patients ((the HAM-D21 score on the 6th month)–(the HAM-D21 score on the 0th month)) and a difference between the number of cells of *Bifidobacterium* on the 0th month and the number of cells of *Bifidobacterium* on the 6th month in the patients ((the number of cells of *Bifidobacterium* on the 6th month)–(the number of cells of *Bifidobacterium* on the 0th month)) were obtained, and the correlation thereof was then analyzed. As a result, it was found that, as the number of cells of *Bifidobacterium* on the 6th month has increased from the number of cells of *Bifidobacterium* on the 0th month in the depression patients, the HAM-D21 score has significantly decreased, and the depressive symptom was alleviated (FIG. 2). Thereby, it was found that there is a correlation between the number of cells of *Bifidobacterium* and the depressive symptom. It is to be noted that, in the present test, the analysis was carried out on 20 depression patients, from whom the specimens could be obtained both on the 0th month and on the 6th month.

2) Manic Depression

In the evaluation according to the self-report measure of stress HSCL described in (4)(b)2), a significant correlation was obtained in manic depression patients, such that as the scores of obsessive symptom, interpersonal hypersensitivity, anxiety symptom, and depressive symptom and the total score have increased, the number of cells of *Bifidobacterium* has decreased, and as the scores have decreased, the number of cells has increased (FIGS. 3 to 7). Specifically, it was found that, regarding obsessive symptom, it can be determined that when the number of cells of *Bifidobacterium* is $10^{9.9}$ cells or more per 1 g of feces, the patient is highly likely to have a mild degree of obsessive symptom, that when the number of cells of *Bifidobacterium* is $10^{9.8}$ to $10^{9.5}$ cells per 1 g of feces, the patient is highly likely to have a moderate degree of obsessive symptom, and that when the number of cells of *Bifidobacterium* is $10^{9.4}$ cells or less per 1 g of feces, the patient is highly likely to have a severe degree of obsessive symptom. It was also found that, regarding interpersonal hypersensitivity, it can be determined that when the number of cells of *Bifidobacterium* is $10^{10.1}$ cells or more per 1 g of feces, the patient is highly likely to have a mild degree of interpersonal hypersensitivity, that when the number of cells of *Bifidobacterium* is $10^{10.0}$ to $10^{9.9}$ cells per 1 g of feces, the patient is highly likely to have a moderate degree of interpersonal hypersensitivity, and that when the number of cells of *Bifidobacterium* is $10^{9.8}$ cells or less per 1 g of feces, the patient is highly likely to have a severe degree of interpersonal hypersensitivity. Moreover, it was also found that, regarding anxiety symptom, it can be determined that when the number of cells of *Bifidobacterium* is $10^{9.7}$ cells or more per 1 g of feces, the patient is highly likely to have a mild degree of anxiety symptom, that when the number of cells of *Bifidobacterium* is $10^{9.6}$ to $10^{9.3}$ cells per 1 g of feces, the patient is highly likely to have a moderate degree of anxiety symptom, and that when the number of cells of *Bifidobacterium* is $10^{9.2}$ cells or less per 1 g of feces, the patient is highly likely to have a severe degree of anxiety symptom. Furthermore, it was also found that, regarding depressive symptom, it can be determined that when the number of cells of *Bifidobacterium* is $10^{9.9}$ cells or more per 1 g of feces, the patient is highly likely to have a mild degree of depressive symptom, that when the number of cells of *Bifidobacterium* is $10^{9.8}$ to $10^{9.4}$ cells per 1 g of feces, the patient is highly likely to have a moderate degree of depressive symptom, and that when the number of cells of *Bifidobacterium* is $10^{9.3}$ cells or less per 1 g of feces, the patient is highly likely to have a severe degree of depressive symptom.

(g) *Bacteroides Fragilis* Group
1) Schizophrenia

In the comparison using a cut-off value described in the above (4)(a)2), when the ratio of schizophrenia patients in which the number of cells of *Bacteroides fragilis* group was less than $10^{9.1}$ cells was compared with the ratio of healthy subjects in which the number of cells of *Bacteroides fragilis* group was less than $10^{9.1}$ cells, the ratio of schizophrenia patients was significantly higher than the ratio of healthy subjects, as shown in Table 16. Accordingly, it was found that when the number of cells of *Bacteroides fragilis* group per 1 g of feces is less than $10^{9.1}$ cells, it can be determined that the subject is highly likely to have schizophrenia.

TABLE 16

| | Cut-off value * | Ratio of less than cut-off value | P value |
|---|---|---|---|
| Healthy subject n = 51 | 9.1 | 7/51 (14%) | P = 0.025 |
| Schizophrenia n = 47 | | 15/47 (32%) | |

* The number of cells per 1 g of feces (Log10 cells/g fecal) is indicated.

(h) *Enterococcus*
1) Depression

In the comparison using a cut-off value described in the above (4)(a)2), when the ratio of depression patients in which the number of cells of *Enterococcus* was less than $10^{7.1}$ cells was compared with the ratio of healthy subjects in which the number of cells of *Enterococcus* was less than $10^{7.1}$ cells, the ratio of depression patients was significantly higher than the ratio of healthy subjects, as shown in Table 17. Accordingly, it was found that when the number of cells of *Enterococcus* per 1 g of feces is less than $10^{7.1}$ cells, it can be determined that the subject is highly likely to have depression.

TABLE 17

| | Cut-off value * | Ratio of less than cut-off value | P value |
|---|---|---|---|
| Healthy subject n = 57 | 7.1 | 48/57 (84%) | P = 0.040 |
| Depression n = 43 | | 42/43 (98%) | |

* The number of cells per 1 g of feces (Log10 cells/g fecal) is indicated.

2) Manic Depression

In the comparison using a cut-off value described in the above (4)(a)2), when the ratio of manic depression patients in which the number of cells of *Enterococcus* was $10^{5.0}$ cells or more was compared with the ratio of healthy subjects in which the number of cells of *Enterococcus* was $10^{5.0}$ cells or more, the ratio of manic depression patients was significantly higher than the ratio of healthy subjects, as shown in Table 18. Accordingly, it was found that when the number of cells of *Enterococcus* per 1 g of feces is $10^{5.0}$ cells or more, it can be determined that the subject is highly likely to have manic depression.

TABLE 18

| | Cut-off value * | Ratio of cut-off value or greater | P value |
|---|---|---|---|
| Healthy subject n = 58 | 5.0 | 37/58 (64%) | P = 0.037 |
| Manic depression n = 39 | | 33/39 (85%) | |

* The number of cells per 1 g of feces (Log10 cells/g fecal) is indicated.

(i) *Clostridium Coccoides* Group
1) Depression

In the comparison with healthy subjects in terms of the number of cells described in the above (4)(a)1), the number of cells of *Clostridium coccoides* group was significantly larger in depression patients than in healthy subjects, as shown in Table 19. In addition, in the comparison using a cut-off value described in the above (4)(a)2), when the ratio of depression patients in which the number of cells of *Clostridium coccoides* group was $10^{10.3}$ cells or more was compared with the ratio of healthy subjects in which the number of cells of *Clostridium coccoides* group was $10^{10.3}$ cells or more, the ratio of depression patients was significantly higher than the ratio of healthy subjects, as shown in Table 20. Accordingly, it was found that when the number of cells of *Clostridium coccoides* group per 1 g of feces is $10^{10.3}$ cells or more, it can be determined that the subject is highly likely to have depression.

TABLE 19

| | Median (minimum value-maximum value)* | P value |
|---|---|---|
| Healthy subject n = 57 | 9.8 (8.7-10.9) | P = 0.007 |
| Depression n = 43 | 10.3 (2.5-11.1) | |

*The number of cells per 1 g of feces (Log10 cells/g fecal) is indicated.

TABLE 20

| | Cut-off value * | Ratio of cut-off value or greater | P value |
|---|---|---|---|
| Healthy subject n = 57 | 10.3 | 9/57 (16%) | P < 0.001 |
| Depression n = 43 | | 24/43 (56%) | |

* The number of cells per 1 g of feces (Log10 cells/g fecal) is indicated.

2) Manic Depression

In the comparison using a cut-off value described in the above (4)(a)2), when the ratio of manic depression patients in which the number of cells of *Clostridium coccoides* group was less than $10^{9.3}$ cells was compared with the ratio of healthy subjects in which the number of cells of *Clostridium coccoides* group was less than $10^{9.3}$ cells, the ratio of manic depression patients was significantly higher than the ratio of healthy subjects, as shown in Table 21. Accordingly, it was found that when the number of cells of *Clostridium coccoides* group per 1 g of feces is less than $10^{9.3}$ cells, it can be determined that the subject is highly likely to have manic depression.

TABLE 21

| | Cut-off value * | Ratio of less than cut-off value | P value |
|---|---|---|---|
| Healthy subject n = 58 | 9.3 | 6/58 (10%) | P = 0.004 |
| Manic depression n = 39 | | 14/39 (36%) | |

* The number of cells per 1 g of feces (Log10 cells/g fecal) is indicated.

3) Schizophrenia

In the comparison using a cut-off value described in the above (4)(a)2), when the ratio of schizophrenia patients in which the number of cells of *Clostridium coccoides* group was less than $10^{9.3}$ cells was compared with the ratio of healthy subjects in which the number of cells of *Clostridium coccoides* group was less than $10^{9.3}$ cells, the ratio of schizophrenia patients was significantly higher than the ratio of healthy subjects, as shown in Table 22. Accordingly, it was found that when the number of cells of *Clostridium coccoides* group per 1 g of feces is less than $10^{9.3}$ cells, it can be determined that the subject is highly likely to have schizophrenia.

TABLE 22

| | Cut-off value * | Ratio of less than cut-off value | P value |
|---|---|---|---|
| Healthy subject n = 51 | 9.3 | 5/51 (10%) | P = 0.020 |
| Schizophrenia n = 47 | | 14/47 (30%) | |

* The number of cells per 1 g of feces (Log10 cells/g fecal) is indicated.

(j) *Clostridium Leptum* Subgroup

1) Depression

In the comparison with healthy subjects in terms of the number of cells described in the above (4)(a)1), the number of cells of *Clostridium leptum* subgroup was significantly larger in depression patients than in healthy subjects, as shown in Table 23. In addition, in the comparison using a cut-off value described in the above (4)(a)2), when the ratio of depression patients in which the number of cells of *Clostridium* leptum subgroup was less than $10^{9.8}$ cells was compared with the ratio of healthy subjects in which the number of cells of *Clostridium leptum* subgroup was less than $10^{9.8}$ cells, the ratio of depression patients was significantly higher than the ratio of healthy subjects, as shown in Table 24. Accordingly, it was found that when the number of cells of *Clostridium leptum* subgroup per 1 g of feces is less than $10^{9.8}$ cells, it can be determined that the subject is highly likely to have depression.

TABLE 23

| | Median (minimum value-maximum value)* | P value |
|---|---|---|
| Healthy subject n = 57 | 10.1 (8.5-11.2) | P = 0.018 |
| Depression n = 43 | 9.8 (6.9-10.8) | |

*The number of cells per 1 g of feces (Log10 cells/g fecal) is indicated.

TABLE 24

| | Cut-off value * | Ratio of less than cut-off value | P value |
|---|---|---|---|
| Healthy subject n = 57 | 9.8 | 17/57 (30%) | P = 0.039 |
| Depression n = 43 | | 22/43 (51%) | |

* The number of cells per 1 g of feces (Log10 cells/g fecal) is indicated.

2) Manic Depression

In the comparison with healthy subjects in terms of the number of cells described in the above (4)(a)1), the number of cells of *Clostridium leptum* subgroup was significantly larger in manic depression patients than in healthy subjects, as shown in Table 25. In addition, in the comparison using a cut-off value described in the above (4)(a)2), when the ratio of manic depression patients in which the number of cells of *Clostridium leptum* subgroup was less than $10^{10.2}$ cells was compared with the ratio of healthy subjects in which the number of cells of *Clostridium leptum* subgroup was less than $10^{10.2}$ cells, the ratio of manic depression patients was significantly higher than the ratio of healthy subjects, as shown in Table 26. Accordingly, it was found that when the number of cells of *Clostridium leptum* subgroup per 1 g of feces is less than $10^{10.2}$ cells, it can be determined that the subject is highly likely to have manic depression.

TABLE 25

| | Median (minimum value-maximum value)* | P value |
|---|---|---|
| Healthy subject n = 58 | 10.1 (8.5-11.2) | P = 0.031 |
| Manic depression n = 39 | 9.9 (7.9-11.1) | |

*The number of cells per 1 g of feces (Log10 cells/g fecal) is indicated.

TABLE 26

| | Cut-off value* | Ratio of less than cut-off value | P value |
|---|---|---|---|
| Healthy subject n = 58 | 10.2 | 31/58 (53%) | P = 0.031 |
| Manic depression n = 39 | | 30/39 (77%) | |

*The number of cells per 1 g of feces (Log10 cells/g fecal) is indicated.

3) Schizophrenia

In the comparison with healthy subjects in terms of the number of cells described in the above (4)(a)1), the number of cells of *Clostridium leptum* subgroup was significantly larger in schizophrenia patients than in healthy subjects, as shown in Table 27. In addition, in the comparison using a cut-off value described in the above (4)(a)2), when the ratio of schizophrenia patients in which the number of cells of *Clostridium leptum* subgroup was less than $10^{9.5}$ cells was compared with the ratio of healthy subjects in which the number of cells of *Clostridium leptum* subgroup was less than $10^{9.5}$ cells, the ratio of schizophrenia patients was significantly higher than the ratio of healthy subjects, as shown in Table 28. Accordingly, it was found that when the number of cells of *Clostridium leptum* subgroup per 1 g of feces is less than $10^{9.5}$ cells, it can be determined that the subject is highly likely to have schizophrenia.

TABLE 27

| | Median (minimum value-maximum value)* | P value |
|---|---|---|
| Healthy subject n = 51 | 10.1 (8.5-11.2) | P = 0.045 |
| Schizophrenia n = 47 | 9.9 (7.6-11.0) | |

*The number of cells per 1 g of feces (Log10 cells/g fecal) is indicated.

TABLE 28

| | Cut-off value* | Ratio of less than cut-off value | P value |
|---|---|---|---|
| Healthy subject n = 51 | 9.5 | 6/51 (12%) | P = 0.025 |
| Schizophrenia n = 47 | | 15/47 (32%) | |

*The number of cells per 1 g of feces (Log10 cells/g fecal) is indicated.

(k) *Staphylococcus*

1) Manic Depression

In the comparison with healthy subjects in terms of the number of cells described in the above (4) (a)1), the number of cells of *Staphylococcus* was significantly smaller in manic depression patients than in healthy subjects, as shown in Table 29. In addition, in the comparison using a cut-off value described in the above (4)(a)2), when the ratio of manic depression patients in which the number of cells of *Staphylococcus* was less than $10^{4.4}$ cells was compared with the ratio of healthy subjects in which the number of cells of *Staphylococcus* was less than $10^{4.4}$ cells, the ratio of manic depression patients was significantly lower than the ratio of healthy subjects, as shown in Table 30. Accordingly, it was found that when the number of cells of *Staphylococcus* per 1 g of feces is less than $10^{4.4}$ cells, it can be determined that the subject is highly likely to have manic depression.

TABLE 29

|  | Median (minimum value-maximum value)* | P value |
|---|---|---|
| Healthy subject n = 58 | 4.6 (1.5-6.1) | P = 0.046 |
| Manic depression n = 39 | 4.2 (1.5-7.4) |  |

*The number of cells per 1 g of feces (Log10 cells/g fecal) is indicated.

TABLE 30

|  | Cut-off value* | Ratio of less than cut-off value | P value |
|---|---|---|---|
| Healthy subject n = 58 | 4.4 | 25/58 (43%) | P = 0.013 |
| Manic depression n = 39 |  | 27/39 (69%) |  |

*The number of cells per 1 g of feces (Log10 cells/g fecal) is indicated.

(1) *Clostridium Perfringens*

1) Depression

In the comparison using a cut-off value described in the above (4) (a)2), when the ratio of depression patients in which the number of cells of *Clostridium perfringens* was less than $10^{2.3}$ cells was compared with the ratio of healthy subjects in which the number of cells of *Clostridium perfringens* was less than $10^{2.3}$ cells, the ratio of depression patients was significantly higher than the ratio of healthy subjects, as shown in Table 31. Accordingly, it was found that when the number of cells of *Clostridium perfringens* per 1 g of feces is less than $10^{2.3}$ cells, it can be determined that the subject is highly likely to have depression.

TABLE 31

|  | Cut-off value* | Ratio of less than cut-off value | P value |
|---|---|---|---|
| Healthy subject n = 57 | 2.3 | 31/57 (54%) | P = 0.035 |
| Depression n = 43 |  | 33/43 (76%) |  |

*The number of cells per 1 g of feces (Log10 cells/g fecal) is indicated.

2) Manic Depression

In the comparison using a cut-off value described in the above (4)(a)2), when the ratio of manic depression patients in which the number of cells of *Clostridium perfringens* was less than $10^{4.0}$ cells was compared with the ratio of healthy subjects in which the number of cells of *Clostridium perfringens* was less than $10^{4.0}$ cells, the ratio of manic depression patients was significantly higher than the ratio of healthy subjects, as shown in Table 32. Accordingly, it was found that when the number of cells of *Clostridium perfringens* per 1 g of feces is less than $10^{4.0}$ cells, it can be determined that the subject is highly likely to have manic depression.

TABLE 32

|  | Cut-off value* | Ratio of less than cut-off value | P value |
|---|---|---|---|
| Healthy subject n = 58 | 4.0 | 37/58 (64%) | P = 0.037 |
| Manic depression n = 39 |  | 33/39 (85%) |  |

*The number of cells per 1 g of feces (Log10 cells/g fecal) is indicated.

3) Schizophrenia

In the comparison using a cut-off value described in the above (4)(a)2), when the ratio of schizophrenia patients in which the number of cells of *Clostridium perfringens* was less than $10^{4.7}$ cells was compared with the ratio of healthy subjects in which the number of cells of *Clostridium perfringens* was less than $10^{4.7}$ cells, the ratio of schizophrenia patients was significantly higher than the ratio of healthy subjects, as shown in Table 33. Accordingly, it was found that when the number of cells of *Clostridium perfringens* per 1 g of feces is less than $10^{4.7}$ cells, it can be determined that the subject is highly likely to have schizophrenia.

TABLE 33

|  | Cut-off value* | Ratio of less than cut-off value | P value |
|---|---|---|---|
| Healthy subject n = 51 | 4.7 | 34/51 (67%) | P = 0.019 |
| Schizophrenia n = 47 |  | 41/47 (87%) |  |

*The number of cells per 1 g of feces (Log10 cells/g fecal) is indicated.

(m) *Enterobacteriaceae*

1) Depression

In the comparison with healthy subjects in terms of the number of cells described in the above (4)(a)1), the number of cells of *Enterobacteriaceae* was significantly smaller in depression patients than in healthy subjects, as shown in Table 34. In addition, in the comparison using a cut-off value described in the above (4)(a)2), when the ratio of depression patients in which the number of cells of *Enterobacteriaceae* was less than $10^{6.4}$ cells was compared with the ratio of healthy subjects in which the number of cells of *Enterobacteriaceae* was less than $10^{6.4}$ cells, the ratio of depression patients was significantly higher than the ratio of healthy subjects, as shown in Table 35. Accordingly, it was found that when the number of cells of *Enterobacteriaceae* per 1 g of feces is less than $10^{6.4}$ cells, it can be determined that the subject is highly likely to have depression.

TABLE 34

|  | Median (minimum value-maximum value)* | P value |
|---|---|---|
| Healthy subject n = 57 | 7.3 (4.2-8.6) | P = 0.010 |
| Depression n = 43 | 6.7 (2.0-8.3) |  |

*The number of cells per 1 g of feces (Log10 cells/g fecal) is indicated.

TABLE 35

|  | Cut-off value* | Ratio of less than cut-off value | P value |
|---|---|---|---|
| Healthy subject n = 57 | 6.4 | 7/57 (12%) | P < 0.001 |
| Depression n = 43 |  | 19/43 (44%) |  |

*The number of cells per 1 g of feces (Log10 cells/g fecal) is indicated.

2) Manic Depression

In the comparison using a cut-off value described in the above (4)(a)2), when the ratio of manic depression patients in which the number of cells of *Enterobacteriaceae* was less than $10^{7.2}$ cells was compared with the ratio of healthy subjects in which the number of cells of *Enterobacteriaceae* was less than $10^{7.2}$ cells, the ratio of manic depression patients was significantly higher than the ratio of healthy subjects, as shown in Table 36. Accordingly, it was found that when the number of cells of *Enterobacteriaceae* per 1 g of feces is less than $10^{7.2}$ cells, it can be determined that the subject is highly likely to have manic depression.

TABLE 36

|  | Cut-off value* | Ratio of less than cut-off value | P value |
|---|---|---|---|
| Healthy subject n = 58 | 7.2 | 27/58 (47%) | P = 0.021 |
| Manic depression n = 39 |  | 28/39 (72%) |  |

*The number of cells per 1 g of feces (Log10 cells/g fecal) is indicated.

3) Schizophrenia

In the comparison using a cut-off value described in the above (4)(a)2), when the ratio of schizophrenia patients in which the number of cells of *Enterobacteriaceae* was less than $10^{6.4}$ cells was compared with the ratio of healthy subjects in which the number of cells of *Enterobacteriaceae* was less than $10^{6.4}$ cells, the ratio of schizophrenia patients was significantly higher than the ratio of healthy subjects, as shown in Table 37. Accordingly, it was found that when the number of cells of *Enterobacteriaceae* per 1 g of feces is less than $10^{6.4}$ cells, it can be determined that the subject is highly likely to have schizophrenia.

TABLE 37

|  | Cut-off value* | Ratio of less than cut-off value | P value |
|---|---|---|---|
| Healthy subject n = 51 | 6.4 | 6/51 (12%) | P = 0.014 |
| Schizophrenia n = 47 |  | 16/47 (34%) |  |

*The number of cells per 1 g of feces (Log10 cells/g fecal) is indicated.

(n) Relationship between Enterobacteria and IBS in Manic Depression Patients

With regard to the manic depression patients described in the above (4)(c), the manic depression patients having IBS were compared with the manic depression patients not having IBS, in terms of the number of cells of *Atopobium* cluster, *Clostridium coccoides* group, and *Staphylococcus*. As a result, it was found that the number of cells of each enterobacterial strain was significantly smaller in the patient having IBS than in the patient not having IBS (Table 38 to Table 40). Thereby, it was found that when the number of cells of *Atopobium* cluster per 1 g of feces is less than $10^{8.8}$ cells, when the number of cells of *Clostridium coccoides* group per 1 g of feces is less than $10^{9.3}$ cells, or when the number of cells of *Staphylococcus* per 1 g of feces is less than $10^{3.5}$ cells, it can be determined that the manic depression patient is highly likely to have IBS.

TABLE 38

|  | Number of cells of Atopobium cluster Median (minimum value-maximum value)* | P value |
|---|---|---|
| Manic depression with IBS n = 10 | 8.8 (7.4-9.9) | P = 0.031 |
| Manic depression without IBS n = 29 | 9.5 (7.9-10.3) |  |

*The number of cells per 1 g of feces (Log10 cells/g fecal) is indicated.

TABLE 39

|  | Number of cells of Clostridium coccoides group Median (minimum value-maximum value)* | P value |
|---|---|---|
| Manic depression with IBS n = 10 | 9.3 (8.7-10.0) | P = 0.020 |
| Manic depression without IBS n = 29 | 9.9 (7.3-11.2) |  |

*The number of cells per 1 g of feces (Log10 cells/g fecal) is indicated.

TABLE 40

|  | Number of cells of Staphylococcus Median (minimum value-maximum value)* | P value |
|---|---|---|
| Manic depression with IBS n = 10 | 3.5 (1.5-5.4) | P = 0.047 |
| Manic depression without IBS n = 29 | 4.3 (1.5-7.4) |  |

*The number of cells per 1 g of feces (Log10 cells/g fecal) is indicated.

The invention claimed is:

1. A method of identifying an agent as highly likely being a mental disease-improving agent, the method comprising:
administering a test substance to a subject,
obtaining a fecal specimen from the subject and a fecal specimen from a subject that has not been administered the test substance,
conducting RNA extraction from the fecal specimens,
measuring the number of enterobacterial cells contained in the fecal specimens by subjecting the extracted RNA to RT-PCR using primers,
comparing the number of enterobacterial cells contained in the fecal specimen of the subject and the number of enterobacterial cells contained in the fecal specimen of the unadministered subject, and
identifying the test substance as an agent which is highly likely a mental disease-improving agent when the test substance has increased the number of the enterobacterial cells, has promoted an increase in the number of the enterobacterial cells, or has suppressed a decrease in the number of the enterobacterial cells in the administered subject compared to the unadministered subject,
wherein the subject is a human, a mouse, a rat, or a rabbit, and
wherein when the mental disease is depression, the enterobacterial cells are cells of *Bifidobacterium* and/or *Lactobacillus*,
wherein when the mental disease is manic depression, the enterobacterial cells are cells of *Staphylococcus*, or
wherein when the mental disease is schizophrenia, the enterobacterial cells are cells of *Lactobacillus sakei* subgroup and/or *Bacteroides fragilis* group,
wherein feces obtained from the following subjects are excluded:
males and females older than or equal to 63 years;
patients with complications of severe medical diseases;
patients taking antibiotics;
patients having intellectual disability, epilepsy, or severe congenital abnormality;
patients with surgical history of intestinal tract;
wherein exclusion criteria minimize the influence of aging, health issues other than a mental disease, and agents that affect the survivability of enterobacteria,
wherein a difference in the numbers of the enterobacterial cells between the subject that has been administered the test substance and the unadministered subject identifies the test substance as highly likely being a mental disease-improving agent.

2. The method of claim 1, wherein the number of cells of *Lactobacillus* is measured using primers having the nucleotide sequences of SEQ ID NOS: 3 to 20, the number of cells of *Lactobacillus sakei* subgroup is measured using primers having the nucleotide sequences of SEQ ID NOS: 13 and 14, the number of cells of *Bifidobacterium* is measured using primers having the nucleotide sequences of SEQ ID NOS: 21 and 22, the number of cells of *Bacteroides fragilis* is measured using primers having the nucleotide sequences of SEQ ID NOS: 23 and 24, and the number of cells of *Staphylococcus* is measured using primers having the nucleotide sequences of SEQ ID NOS: 31 and 32.

3. A method for determining severity of a mental disease in a subject having the mental disease the method comprising:
obtaining a fecal specimen from a subject,
conducting RNA extraction from the fecal specimen,
measuring the number of enterobacterial cells contained in the fecal specimen of the subject by subjecting the extracted RNA to RT-PCR using primers,
wherein when the mental disease is depression, the enterobacterial cells are cells of *Lactobacillus*; or
wherein when the mental disease is manic depression, the enterobacterial cells are cells of *Bifidobacterium*;
determining that an anxiety symptom is of a mild degree when the number of cells of *Lactobacillus* per 1 g of the feces specimen is $10^{6.5}$ cells or more, an anxiety symptom is of a moderate degree when the number of cells of *Lactobacillus* per 1 g of the feces specimen is $10^{6.4}$ to $10^{5.8}$ cells, or an anxiety symptom of a severe degree when the number of cells of *Lactobacillus* per 1 g of the feces specimen is $10^{5.7}$ cells or less,
wherein the subject is a depression patient having the anxiety symptom;
determining that an obsessive symptom is of a mild degree when the number of cells of *Bifidobacterium* per 1 g of the feces specimen is $10^{9.9}$ cells or more, an obsessive symptom is of a moderate degree when the number of cells of *Bifidobacterium* per 1 g of the feces specimen is $10^{9.8}$ to $10^{9.5}$ cells, or an obsessive symptom is of a severe degree when the number of cells of Bifidobacterium per 1 g of the feces specimen is $10^{9.4}$ cells or less;

determining that interpersonal hypersensitivity is of a mild degree when the number of cells of Bifidobacterium per 1 g of the feces specimen is $10^{10.1}$ cells or more, interpersonal hypersensitivity is of a moderate degree when the number of cells of Bifidobacterium per 1 g of the feces specimen is $10^{10.0}$ to $10^{9.9}$ cells, or interpersonal hypersensitivity is of a severe degree when the number of cells of Bifidobacterium per 1 g of the feces specimen is $10^{9.8}$ cells or less;

determining that an anxiety symptom is of a mild degree when the number of cells of Bifidobacterium per 1 g of the feces specimen is $10^{9.7}$ cells or more, an anxiety symptom is of a moderate degree when the number of cells of Bifidobacterium per 1 g of the feces specimen is $10^{9.6}$ to $10^{9.3}$ cells, or an anxiety symptom is of a severe degree when the number of cells of Bifidobacterium per 1 g of the feces specimen is $10^{9.2}$ cells or less; or determining that a depressive symptom is of a mild degree when the number of cells of Bifidobacterium per 1 g of the feces specimen is $10^{9.9}$ cells or more, a depressive symptom is of a moderate degree when the number of cells of Bifidobacterium per 1 g of the feces specimen is $10^{9.8}$ to $10^{9.4}$ cells, or a depressive symptom is of a severe degree when the number of cells of Bifidobacterium per 1 g of the feces specimen is $10^{9.3}$ cells or less, wherein the subject is a manic depression patient, and wherein the number of cells of Lactobacillus is measured using primers having the nucleotide sequences of SEQ ID NOS: 3 to 20, and the number of cells of Bifidobacterium is measured using primers having the nucleotide sequences of SEQ ID NOS: 21 and 22, wherein feces obtained from the following subjects are excluded:

males and females older than or equal to 63 years;
patients with complications of severe medical diseases;
patients taking antibiotics;
patients having intellectual disability, epilepsy, or severe congenital abnormality;
patients with surgical history of intestinal tract;
wherein exclusion criteria minimize the influence of aging, health issues other than a mental disease, and agents that affect the survivability of enterobacteria.

4. A method of determining the number of enterobacterial cells in a subject, the method comprising:

obtaining a fecal specimen from a healthy subject and a fecal specimen from a subject diagnosed to have a mental disease,
conducting RNA extraction from the fecal specimens,
measuring the number of enterobacterial cells contained in the fecal specimens by subjecting the extracted RNA to RT-PCR using primers, wherein the number of cells of Lactobacillus is measured using primers having the nucleotide sequences of SEQ ID NOS: 3 to 20, the number of cells of Lactobacillus saltier subgroup is measured using primers having the nucleotide sequences of SEQ ID NOS: 13 and 14, the number of cells of Bifidobacterium is measured using primers having the nucleotide sequences of SEQ ID NOS: 21 and 22, the number of cells of Bacteroides fragilis is measured using primers having the nucleotide sequences of SEQ ID NOS: 23 and 24, and the number of cells of Staphylococcus is measured using primers having the nucleotide sequences of SEQ ID NOS: 31 and 32, examining a difference between the number of cells of each enterobacterial strain in the subject diagnosed to have the mental disease and the number of cells of each enterobacterial strain in the healthy subject by applying a Mann-Whitney u-test, carrying out a Receiver Operating analysis (ROC), and obtaining a cut-off value which identifies the number of cells of each enterobacterial strain in the subject diagnosed to have the mental disease and in the healthy subject, obtaining a fecal specimen from another subject,
conducting RNA extraction from the fecal specimen from another subject,
measuring the number of enterobacterial cells contained in the fecal specimen from another subject by subjecting the extracted RNA from the fecal specimen from another subject to RT-PCR using the primers, and
comparing the number of the cells in the another subject and the cut-off value, thereby determine if the another subject has the mental disease, wherein when the mental disease is depression, the enterobacterial cells are cells of Bifidobacterium and/or Lactobacillus,
wherein when the mental disease is manic depression, the enterobacterial cells are cells of Staphylococcus, or
wherein when the mental disease is schizophrenia, the enterobacterial cells are cells of Lactobacillus sakei subgroup and/or Bacteroides group, wherein feces obtained from the following subjects are excluded:
males and females older than or equal to 63 years;
patients with complications of severe medical diseases;
patients taking antibiotics;
patients having intellectual disability, epilepsy, or severe congenital abnormality;
patients with surgical history of intestinal tract;
wherein exclusion criteria are set to minimize the influence of aging, health issues other than a mental disease, and agents that affect the survivability of enterobacteria, wherein criteria of the healthy subject and the subject diagnosed to have a mental disease have been adjusted so that the only significant difference between the healthy and diseased subjects was a mental state and a difference of the numbers of the enterobacterial cells between the subjects was due to the mental state differences between the healthy and diseased subjects.

5. A method for determining that a subject highly likely has a mental disease, the method comprising:

obtaining a fecal specimen from a subject,
conducting RNA extraction from the fecal specimen,
measuring the number of enterobacterial cells contained in the fecal specimen of the subject by subjecting the extracted RNA to RT-PCR using primers,
wherein when the mental disease is depression, the enterobacterial cells are cells of Bifidobacterium and/or Lactobacillus,
wherein when the mental disease is manic depression, the enterobacterial cells are cells of Staphylococcus, or
wherein when the mental disease is schizophrenia, the enterobacterial cells are cells of Lactobacillus sakei subgroup and/or Bacteroides group; and
determining that the subject highly likely has depression when the number of cells of Lactobacillus per 1 g of the feces specimen is less than $10^{6.5}$ cells or the number of cells of *Bifidobacterium* per 1 g of the feces specimen is less than $10^{10.1}$ cells;

determining that the subject highly likely has manic depression when the number of cells of *Staphylococcus* per 1 g of the feces specimen is less than $10^{4.4}$ cells; or determining that the subject highly likely has schizophrenia when the number of cells of *Lactobacillus sakei* subgroup per 1 g of the feces specimen is less than $10^{4.8}$ cells or the number of cells of *Bacteroides fragilis* group per 1 g of the feces specimen is less than $10^{9.1}$ cells, and wherein the number of cells of *Lactobacillus* is measured using primers having the nucleotide sequences of SEQ ID NOS: 3 to 20, the number of cells of *Lactobacillus sakei* subgroup is measured using primers having the nucleotide sequences of SEQ ID NOS: 13 and 14, the number of cells of *Bifidobacterium* is measured using primers having the nucleotide sequences of SEQ ID NOS: 21 and 22, the number of cells of *Bacteroides fragilis* is measured using primers having the nucleotide sequences of SEQ ID NOS: 23 and 24, and the number of cells of *Staphylococcus* is measured using primers having the nucleotide sequences of SEQ ID NOS: 31 and 32, wherein feces obtained from the following subjects are excluded:

males and females older than or equal to 63 years;
patients with complications of severe medical diseases;
patients taking antibiotics;
patients having intellectual disability, epilepsy, or severe congenital abnormality;
patients with surgical history of intestinal tract;
wherein exclusion criteria minimize the influence of aging, health issues other than a mental disease, and agents that affect the survivability of enterobacteria.

* * * * *

SEQUENCE LISTING

```
<160> NUMBER OF SEQ ID NOS: 36

<210> SEQ ID NO 1
<211> LENGTH: 17
<212> TYPE: DNA
<213> ORGANISM: Artificial Sequence
<220> FEATURE:
<223> OTHER INFORMATION: Designed primer based on Atopobium cluster

<400> SEQUENCE: 1
gggttgagag accgacc                                                        17

<210> SEQ ID NO 2
<211> LENGTH: 18
<212> TYPE: DNA
<213> ORGANISM: Artificial Sequence
<220> FEATURE:
<223> OTHER INFORMATION: Designed primer based on Atopobium cluster

<400> SEQUENCE: 2
```
cggrgcttct tctgcagg                                           18

<210> SEQ ID NO 3
<211> LENGTH: 17
<212> TYPE: DNA
<213> ORGANISM: Artificial Sequence
<220> FEATURE:
<223> OTHER INFORMATION: Designed primer based on Lactobacillus

<400> SEQUENCE: 3
accgcatggt tcttggc                                            17

<210> SEQ ID NO 4
<211> LENGTH: 20
<212> TYPE: DNA
<213> ORGANISM: Artificial Sequence
<220> FEATURE:
<223> OTHER INFORMATION: Designed primer based on Lactobacillus

<400> SEQUENCE: 4
ccgacaacag ttactctgcc                                         20

<210> SEQ ID NO 5
<211> LENGTH: 27
<212> TYPE: DNA
<213> ORGANISM: Artificial Sequence
<220> FEATURE:
<223> OTHER INFORMATION: Designed primer based on Lactobacillus

<400> SEQUENCE: 5
gatgcatagc cgagttgaga gactgat                                 27

<210> SEQ ID NO 6
<211> LENGTH: 25
<212> TYPE: DNA
<213> ORGANISM: Artificial Sequence
<220> FEATURE:
<223> OTHER INFORMATION: Designed primer based on Lactobacillus

<400> SEQUENCE: 6
taaaggccag ttactacctc tatcc                                   25

<210> SEQ ID NO 7
<211> LENGTH: 25
<212> TYPE: DNA
<213> ORGANISM: Artificial Sequence
<220> FEATURE:
<223> OTHER INFORMATION: Designed primer based on Lactobacillus

<400> SEQUENCE: 7
ctctggtatt gattggtgct tgcat                                   25

<210> SEQ ID NO 8
<211> LENGTH: 24
<212> TYPE: DNA
<213> ORGANISM: Artificial Sequence
<220> FEATURE:
<223> OTHER INFORMATION: Designed primer based on Lactobacillus

<400> SEQUENCE: 8
gttcgccact cactcaaatg taaa                                    24

<210> SEQ ID NO 9
<211> LENGTH: 16
<212> TYPE: DNA

```
<213> ORGANISM: Artificial Sequence
<220> FEATURE:
<223> OTHER INFORMATION: Designed primer based on Lactobacillus

<400> SEQUENCE: 9
gaacgcaytg gcccaa                                                         16

<210> SEQ ID NO 10
<211> LENGTH: 19
<212> TYPE: DNA
<213> ORGANISM: Artificial Sequence
<220> FEATURE:
<223> OTHER INFORMATION: Designed primer based on Lactobacillus

<400> SEQUENCE: 10
tccattgtgg ccgatcagt                                                      19

<210> SEQ ID NO 11
<211> LENGTH: 21
<212> TYPE: DNA
<213> ORGANISM: Artificial Sequence
<220> FEATURE:
<223> OTHER INFORMATION: Designed primer based on Lactobacillus

<400> SEQUENCE: 11
caccgaatgc ttgcaytcac c                                                   21

<210> SEQ ID NO 12
<211> LENGTH: 19
<212> TYPE: DNA
<213> ORGANISM: Artificial Sequence
<220> FEATURE:
<223> OTHER INFORMATION: Designed primer based on Lactobacillus

<400> SEQUENCE: 12
gccgcgggtc catccaaaa                                                      19

<210> SEQ ID NO 13
<211> LENGTH: 22
<212> TYPE: DNA
<213> ORGANISM: Artificial Sequence
<220> FEATURE:
<223> OTHER INFORMATION: Designed primer based on Lactobacillus

<400> SEQUENCE: 13
cataaaacct amcaccgcat gg                                                  22

<210> SEQ ID NO 14
<211> LENGTH: 27
<212> TYPE: DNA
<213> ORGANISM: Artificial Sequence
<220> FEATURE:
<223> OTHER INFORMATION: Designed primer based on Lactobacillus

<400> SEQUENCE: 14
tcagttacta tcagatacrt tcttctc                                             27

<210> SEQ ID NO 15
<211> LENGTH: 24
<212> TYPE: DNA
<213> ORGANISM: Artificial Sequence
<220> FEATURE:
<223> OTHER INFORMATION: Designed primer based on Lactobacillus

<400> SEQUENCE: 15
attttgtttg aaaggtggct tcgg                                                24
```

-continued

<210> SEQ ID NO 16
<211> LENGTH: 25
<212> TYPE: DNA
<213> ORGANISM: Artificial Sequence
<220> FEATURE:
<223> OTHER INFORMATION: Designed primer based on Lactobacillus

<400> SEQUENCE: 16
acccttgaac agttactctc aaagg                                    25

<210> SEQ ID NO 17
<211> LENGTH: 23
<212> TYPE: DNA
<213> ORGANISM: Artificial Sequence
<220> FEATURE:
<223> OTHER INFORMATION: Designed primer based on Lactobacillus

<400> SEQUENCE: 17
cctgattgat tttggtcgcc aac                                      23

<210> SEQ ID NO 18
<211> LENGTH: 26
<212> TYPE: DNA
<213> ORGANISM: Artificial Sequence
<220> FEATURE:
<223> OTHER INFORMATION: Designed primer based on Lactobacillus

<400> SEQUENCE: 18
acgtatgaac agttactctc atacgt                                   26

<210> SEQ ID NO 19
<211> LENGTH: 19
<212> TYPE: DNA
<213> ORGANISM: Artificial Sequence
<220> FEATURE:
<223> OTHER INFORMATION: Designed primer based on Lactobacillus

<400> SEQUENCE: 19
tgcgcctaat gatagttga                                           19

<210> SEQ ID NO 20
<211> LENGTH: 19
<212> TYPE: DNA
<213> ORGANISM: Artificial Sequence
<220> FEATURE:
<223> OTHER INFORMATION: Designed primer based on Lactobacillus

<400> SEQUENCE: 20
gataccgtcg cgacgtgag                                           19

<210> SEQ ID NO 21
<211> LENGTH: 17
<212> TYPE: DNA
<213> ORGANISM: Artificial Sequence
<220> FEATURE:
<223> OTHER INFORMATION: Designed primer based on Bifidobacterium

<400> SEQUENCE: 21
ctcctggaaa cgggtgg                                             17

<210> SEQ ID NO 22
<211> LENGTH: 22
<212> TYPE: DNA
<213> ORGANISM: Artificial Sequence
<220> FEATURE:

```
<223> OTHER INFORMATION: Designed primer based on Bifidobacterium

<400> SEQUENCE: 22
ggtgttcttc ccgatatcta ca                                             22

<210> SEQ ID NO 23
<211> LENGTH: 21
<212> TYPE: DNA
<213> ORGANISM: Artificial Sequence
<220> FEATURE:
<223> OTHER INFORMATION: Designed primer based on Bacteroides fragilis
      group

<400> SEQUENCE: 23
ayagcctttc gaaagraaga t                                              21

<210> SEQ ID NO 24
<211> LENGTH: 21
<212> TYPE: DNA
<213> ORGANISM: Artificial Sequence
<220> FEATURE:
<223> OTHER INFORMATION: Designed primer based on Bacteroides fragilis
      group

<400> SEQUENCE: 24
ccagtatcaa ctgcaatttt a                                              21

<210> SEQ ID NO 25
<211> LENGTH: 20
<212> TYPE: DNA
<213> ORGANISM: Artificial Sequence
<220> FEATURE:
<223> OTHER INFORMATION: Designed primer based on Enterococcus

<400> SEQUENCE: 25
atcagagggg gataacactt                                                20

<210> SEQ ID NO 26
<211> LENGTH: 21
<212> TYPE: DNA
<213> ORGANISM: Artificial Sequence
<220> FEATURE:
<223> OTHER INFORMATION: Designed primer based on Enterococcus

<400> SEQUENCE: 26
actctcatcc ttgttcttct c                                              21

<210> SEQ ID NO 27
<211> LENGTH: 20
<212> TYPE: DNA
<213> ORGANISM: Artificial Sequence
<220> FEATURE:
<223> OTHER INFORMATION: Designed primer based on Clostridium coccoides
      group

<400> SEQUENCE: 27
aaatgacggt acctgactaa                                                20

<210> SEQ ID NO 28
<211> LENGTH: 22
<212> TYPE: DNA
<213> ORGANISM: Artificial Sequence
<220> FEATURE:
<223> OTHER INFORMATION: Designed primer based on Clostridium coccoides
      group

<400> SEQUENCE: 28
```
ctttgagttt cattcttgcg aa                                              22

<210> SEQ ID NO 29
<211> LENGTH: 16
<212> TYPE: DNA
<213> ORGANISM: Artificial Sequence
<220> FEATURE:
<223> OTHER INFORMATION: Designed primer based on Clostridium leptum
      subgroup

<400> SEQUENCE: 29
gcacaagcag tggagt                                                     16

<210> SEQ ID NO 30
<211> LENGTH: 18
<212> TYPE: DNA
<213> ORGANISM: Artificial Sequence
<220> FEATURE:
<223> OTHER INFORMATION: Designed primer based on Clostridium leptum
      subgroup

<400> SEQUENCE: 30
cttcctccgt tttgtcaa                                                   18

<210> SEQ ID NO 31
<211> LENGTH: 30
<212> TYPE: DNA
<213> ORGANISM: Artificial Sequence
<220> FEATURE:
<223> OTHER INFORMATION: Designed primer based on Staphylococcus

<400> SEQUENCE: 31
tttgggctac acacgtgcta caatggacaa                                      30

<210> SEQ ID NO 32
<211> LENGTH: 24
<212> TYPE: DNA
<213> ORGANISM: Artificial Sequence
<220> FEATURE:
<223> OTHER INFORMATION: Designed primer based on Staphylococcus

<400> SEQUENCE: 32
aacaacttta tgggatttgc wtga                                            24

<210> SEQ ID NO 33
<211> LENGTH: 18
<212> TYPE: DNA
<213> ORGANISM: Artificial Sequence
<220> FEATURE:
<223> OTHER INFORMATION: Designed primer based on Clostridium
      perfringens

<400> SEQUENCE: 33
gggggtttca acacctcc 18

<210> SEQ ID NO 34
<211> LENGTH: 18
<212> TYPE: DNA
<213> ORGANISM: Artificial Sequence
<220> FEATURE:
<223> OTHER INFORMATION: Designed primer based on Clostridium perfringens

<400> SEQUENCE: 34
gcaagggatg tcaagtgt 18

```
<210> SEQ ID NO 35
<211> LENGTH: 23
<212> TYPE: DNA
<213> ORGANISM: Artificial Sequence
<220> FEATURE:
<223> OTHER INFORMATION: Designed primer based on Enterobacteriaceae

<400> SEQUENCE: 35
tgccgtaact cgggagaag gca                                        23

<210> SEQ ID NO 36
<211> LENGTH: 22
<212> TYPE: DNA
<213> ORGANISM: Artificial Sequence
<220> FEATURE:
<223> OTHER INFORMATION: Designed primer based on Enterobacteriaceae

<400> SEQUENCE: 36
tcaaggacca gtgttcagtg tc                                        22
```